US010918480B2

(12) United States Patent
Keränen

(10) Patent No.: US 10,918,480 B2
(45) Date of Patent: Feb. 16, 2021

(54) MEDICAL DEVICE FOR A CARDIAC VALVE IMPLANT, AND A METHOD OF MANUFACTURING THE MEDICAL DEVICE

(71) Applicant: Medtentia International Ltd. Oy, Helsinki (FI)

(72) Inventor: Olli Keränen, Bjärred (SE)

(73) Assignee: Medtentia International Ltd. Oy, Helsinki (FI)

( * ) Notice: Subject to any disclaimer, the term of this patent is extended or adjusted under 35 U.S.C. 154(b) by 420 days.

(21) Appl. No.: 14/441,101

(22) PCT Filed: Nov. 6, 2013

(86) PCT No.: PCT/EP2013/073137
§ 371 (c)(1),
(2) Date: May 6, 2015

(87) PCT Pub. No.: WO2014/072328
PCT Pub. Date: May 15, 2014

(65) Prior Publication Data
US 2015/0265403 A1    Sep. 24, 2015

Related U.S. Application Data

(60) Provisional application No. 61/723,344, filed on Nov. 7, 2012.

(30) Foreign Application Priority Data

Nov. 7, 2012  (EP) ...................................... 12191641

(51) Int. Cl.
*A61F 2/24*    (2006.01)
*B26F 1/32*    (2006.01)

(52) U.S. Cl.
CPC .......... *A61F 2/2427* (2013.01); *A61F 2/2466* (2013.01); *B26F 1/32* (2013.01);
(Continued)

(58) Field of Classification Search
CPC .... A61F 2/2427; A61F 2/2445; A61F 2/2448; A61F 2/2466
See application file for complete search history.

(56) References Cited

U.S. PATENT DOCUMENTS 4,585,453 A    4/1986  Martin et al.
5,972,030 A   10/1999  Garrison et al.
(Continued)

FOREIGN PATENT DOCUMENTS

WO    WO2005/112832 A1    12/2005

OTHER PUBLICATIONS

WIPO, European International Search Authority, International Preliminary Report On Patentability dated May 21, 2015 in International Patent Application No. PCT/EP2013/073137, 7 pages.
(Continued)

*Primary Examiner* — Sarah A Simpson
(74) *Attorney, Agent, or Firm* — Patent Grove LLC; Tomas Friend

(57) ABSTRACT

A medical device (1300) for holding an annuloplasty ring (101) is disclosed comprising a support (102) defining first and second peripheral edges (103, 126) each with a curvature about which said cardiac valve implant can be fitted, wherein the support comprises a grip section (128, 129) positioned between and connected with the first and second peripheral edges at opposite sides of the grip section, the grip section defining an opening for engagement with a gripper tool in use of the support, wherein said grip section is recessed inwards from either of said first and second peripheral edges thereby defining said opening between said
(Continued)

support and said cardiac valve implant when held in place by said support. A method of manufacturing a medical device is disclosed.

17 Claims, 19 Drawing Sheets

(52) U.S. Cl.
CPC ........... *A61F 2/2445* (2013.01); *A61F 2/2448* (2013.01); *A61F 2230/0091* (2013.01); *A61F 2240/001* (2013.01); *A61F 2250/006* (2013.01)

(56) References Cited

U.S. PATENT DOCUMENTS

| | | | | |
|---|---|---|---|---|
| 6,458,867 B1 * | 10/2002 | Wang | ................... | A61L 29/085 523/105 |
| 8,920,493 B2 * | 12/2014 | Brown | .................. | A61F 2/2466 623/2.11 |
| 2003/0176916 A1 * | 9/2003 | Ryan | ..................... | A61F 2/2448 623/2.11 |
| 2004/0034410 A1 | 2/2004 | Holmberg | | |
| 2007/0156234 A1 * | 7/2007 | Adzich | ................. | A61F 2/2466 623/2.11 |
| 2014/0081394 A1 * | 3/2014 | Keranen | ............... | A61F 2/2409 623/2.38 |

OTHER PUBLICATIONS

WIPO, European International Search Authority, International Search Report and Written Opinion dated Jan. 27, 2014 in International Patent Application No. PCT/EP2013/073137, 10 pages.

* cited by examiner

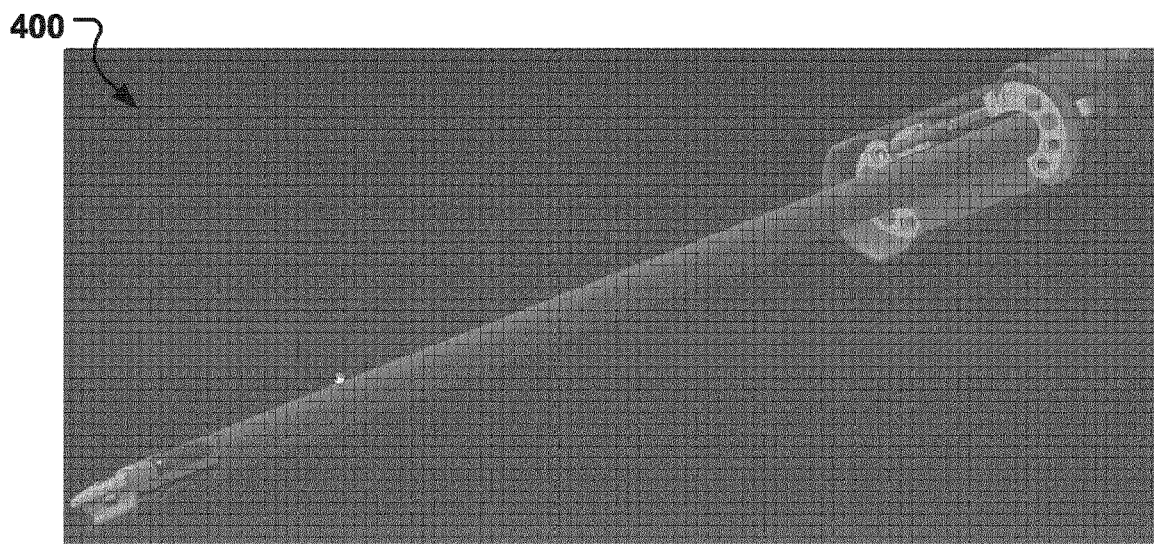
Fig. 22a
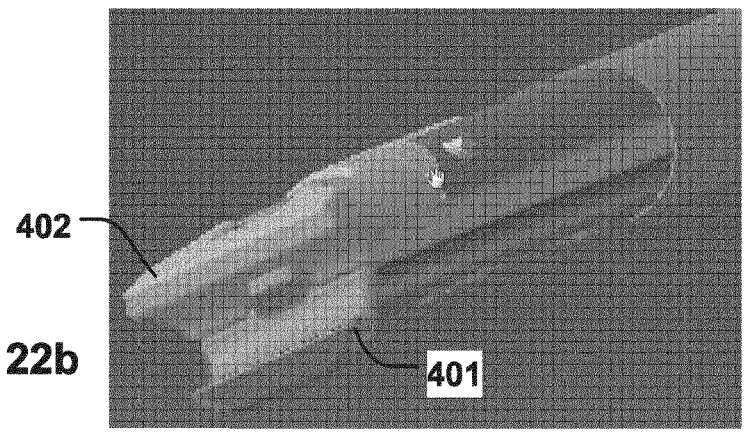
Fig. 22b
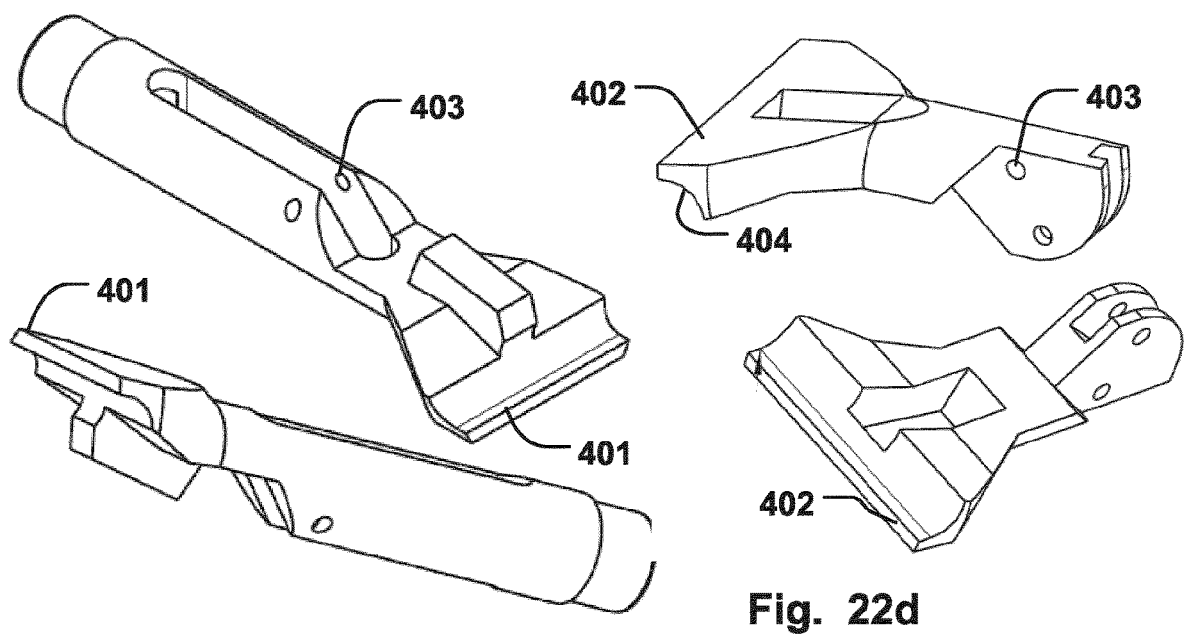
Fig. 22c
Fig. 22d

MEDICAL DEVICE FOR A CARDIAC VALVE IMPLANT, AND A METHOD OF MANUFACTURING THE MEDICAL DEVICE

RELATED APPLICATIONS

This application is the U.S. National Phase of and claims priority to International Patent Application No. PCT/EP2013/073137, International Filing Date Nov. 6, 2013, entitled Medical Device For A Cardiac Valve Implant, And A Method [sic] Of Manufacturing The Medical Device, which claims benefit of European Application No. EP12191641.5, filed Nov. 7, 2012 entitled Medical Device For A Cardiac Valve Implant, And A Method [sic] Of Manufacturing The Medical Device; and U.S. Provisional Application Ser. No. 61/723,344, filed Nov. 7, 2012 entitled Medical Device For A Cardiac Valve Implant, And A Method [sic] Of Manufacturing The Medical Device; all of which are incorporated herein by reference in their entireties.

FIELD OF THE INVENTION

This invention pertains in general to the field of cardiac valve replacement and repair. More particularly the invention relates to a medical device for holding a cardiac valve implant, a kit comprising a tool for manipulation of such medical device, and a method of manufacturing the medical device.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. Such annuloplasty rings or other annuloplasty implants or cardiac valve implants in general such as replacement valves, are put into position by various tools.

An assembly for holding an annuloplasty ring in place for placing a suture line and attach the ring to the annulus tissue is disclosed in U.S. Pat. No. 6,197,052. The annuloplasty ring or suture guide is releasably attached to a guide mount by sutures or threads passing through apertures disposed in the guide mount and through the ring. Once the surgeon is ready to release the ring, the sutures for fixing the ring to the mount are cut of at various locations of the mount, and the guide can subsequently be retrieved. The mount is attachable to a handle assembly which is mounted by inserting a cylindrical hub of the handle assembly into a plug of the mount.

United states patent application US2003176916 discloses a holder for an annuloplasty prosthesis having a first component, around which the prosthesis is mounted and a second component, releasably secured to the first component by sutures. Projections align the two holder components to each other, and a further rectangular projection at the second component is required to prevent deformation and reduction of the circumference of the first holder component which is an open ring. I.e. the first holder component can not satisfactory hold the prosthesis without the second holder component. In some embodiments, rather than retaining the prosthesis to the holder by means of sutures passing through the prosthesis, the prosthesis is retained by means of downwardly extending penetrating members such as barbs, pins, pegs, or needles.

Hence, a problem with prior art devices is the risk of damaging the implant due to complicated mechanisms for attachment and detachment to the holder, thereby increasing the amount of manipulation of the implant both during the positioning phase and during repositioning, which may lead to unnecessary wear and risk of damages to the implant.

During heart surgery, a premium is placed on reducing the amount of time used to replace and repair valves as the heart is frequently arrested and without perfusion. A problem with prior art devices is the time consuming attachment or detachment of the annuloplasty device, also referred to as the cardiac valve implant, or simply implant below, to the holder assembly, e.g. by using sutures. It would therefore be very useful to have a medical device for holding the implant to be positioned at the annulus that can be quickly attached or detached to such implant.

If repositioning of the cardiac valve implant becomes necessary it is also critical that the holder can engage the implant easily and quickly. The suture attachment in prior art devices is complicated and time consuming when such repositioning is required.

Another problem with prior art devices is insufficient visibility through the holder and into the annulus due to complex holder construction with elements extending across the annulus and thereby obscuring the sight. Reduced visibility makes accurate positioning more complicated and time consuming with potentially increased risk.

A further problem with prior art devices is insufficient maneuverability of the cardiac valve implant due to lack of freedom of movement between the holder and the delivery tool. Such lack of flexibility also increases the time of the replacement or repair procedure.

Another problem with prior art holders is the limited ability to adapt to implants having a wide range of sizes. It is therefore necessary to have a number of various holders which complicates the procedure further as frequent exchange of holders may be necessary to find the correct fit.

Another problem with prior art devices is the few options to manipulate the implant via the holder, once the implant is held in place by the holder, i.e. lack of versatility in handling the holder to get the desired course of positioning of the implant, while keeping the holder compact e.g. to maintaining a good view trough the holder during the positioning.

The above problems may have dire consequences for the patient and the health care system. Patient risk is increased.

Hence, an improved medical device for holding a cardiac valve implant would be advantageous and in particular allowing for increased flexibility, reducing the time of lengthy surgery procedures, cost-effectiveness, and increased patient safety. Also, a method of holding a cardiac valve implant with such medical device and a kit comprising a tool for manipulation of such medical device would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a medical device for holding a cardiac valve implant is provided comprising a support defining first and second peripheral edges each with a curvature about which said cardiac valve implant can be fitted, wherein the support comprises a grip section positioned between and connected with the first and second peripheral edges at opposite sides of the grip section, the grip section defining an opening for engagement with a gripper tool in use of the support, wherein said grip section is recessed inwards from either of said first and second peripheral edges thereby defining said opening between said support and said cardiac valve implant when held in place by said support.

According to a second aspect of the invention a kit is provided comprising a medical device according to the first aspect having a grip section and a tool comprising a grip member arranged for gripping of said grip section.

According to a third aspect of the invention a method of manufacturing a medical device for holding a cardiac valve implant is provided, the method comprises providing a sheet of bulk material such as a polymer material, providing a template of the medical device, and punching the sheet with the template to provide the medical device comprising a support defining first and second peripheral edges each with a curvature about which the cardiac valve implant can be fitted, and a grip section for engagement with a gripper tool in use of the support.

Further embodiments of the invention are defined in the dependent claims, wherein features for the second and subsequent aspects of the invention are as for the first aspect mutatis mutandis.

Some embodiments of the invention provide for less time consuming positioning of cardiac valve implants at a target site in the heart.

Some embodiments of the invention provide for less time consuming attachment and detachment of a cardiac valve implant to a medical device for efficient positioning and repositioning of such implant at the annulus.

Some embodiments of the invention provide for flexible positioning of a cardiac valve implant at a target site by conforming to varying anatomical sites in a body.

Some embodiments of the invention provide for increased visibility through the cardiac valve implant and into the annulus for accurate positioning and reducing the risk of complications.

Some embodiments of the invention also provide for a reduced risk of damaging the cardiac valve implant during a repair or replacement procedure.

Some embodiments of the invention provide for a compact holder of a cardiac valve implant with maintained flexibility of positioning.

Some embodiments of the invention provide for a flexible holder in terms of adapting to a wide range of sizes of cardiac valve implants to be positioned.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 22*a-d* are illustrations of a gripper tool according to an embodiment of the invention.

DESCRIPTION OF EMBODIMENTS

Figure 1A:
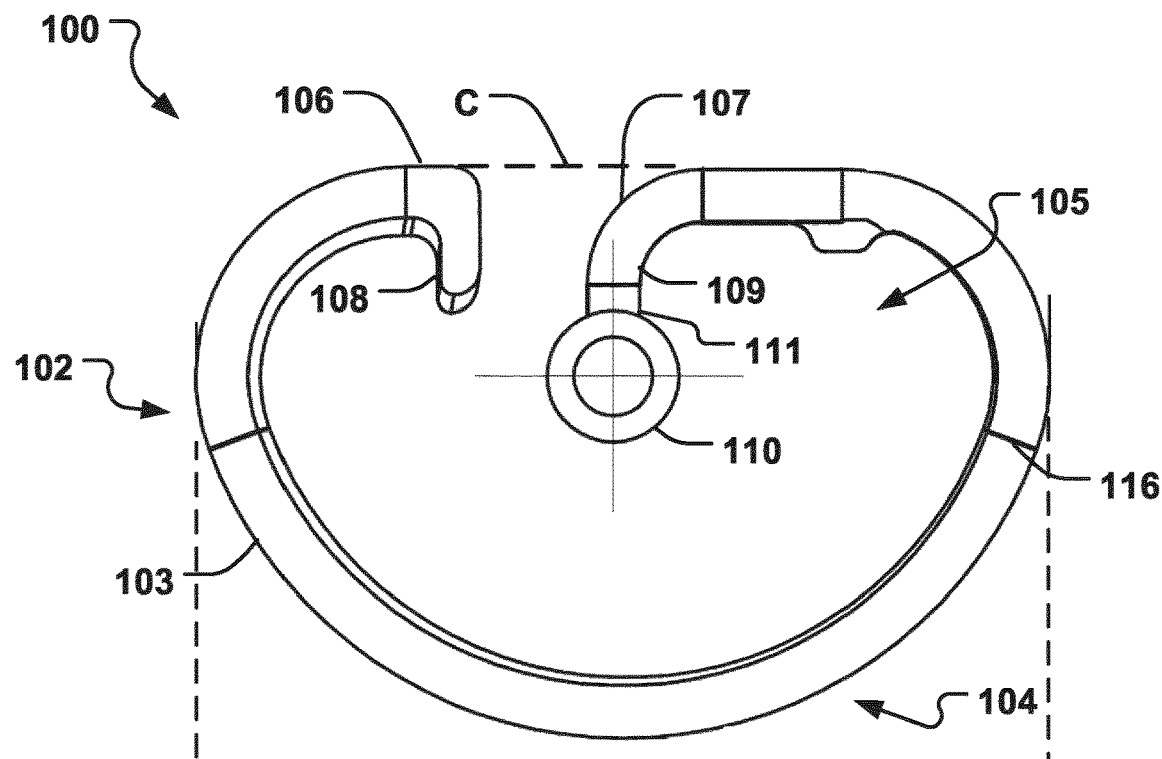
FIGS. 1a-b are illustrations of a medical device according to an embodiment of the invention in a first configuration (a) and in a second configuration (b)

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 1B:
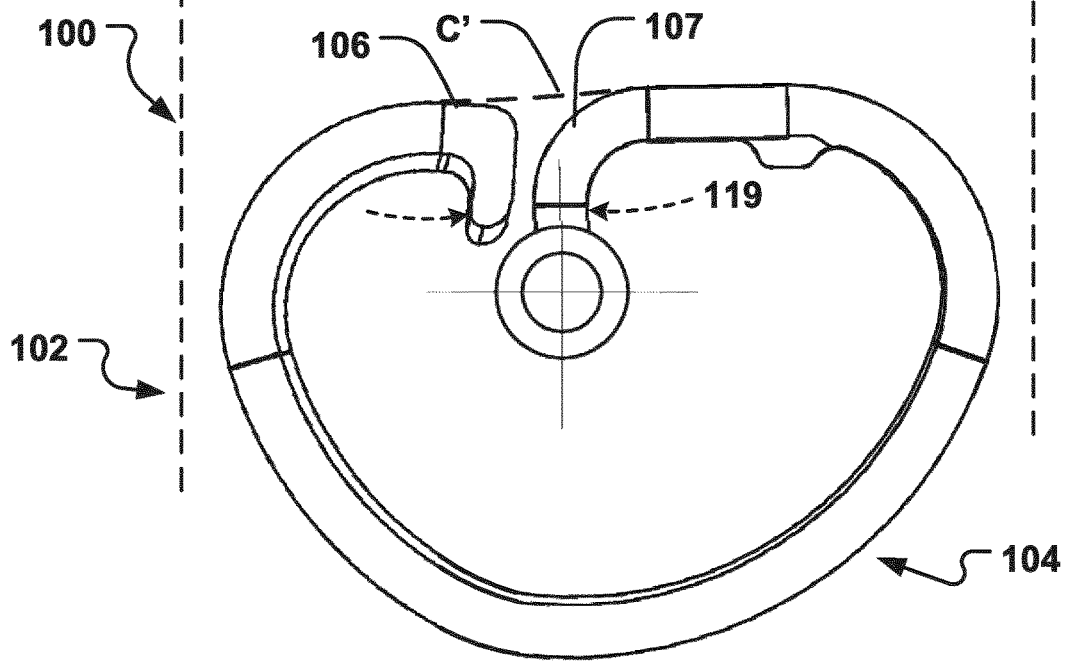
Figure 2:
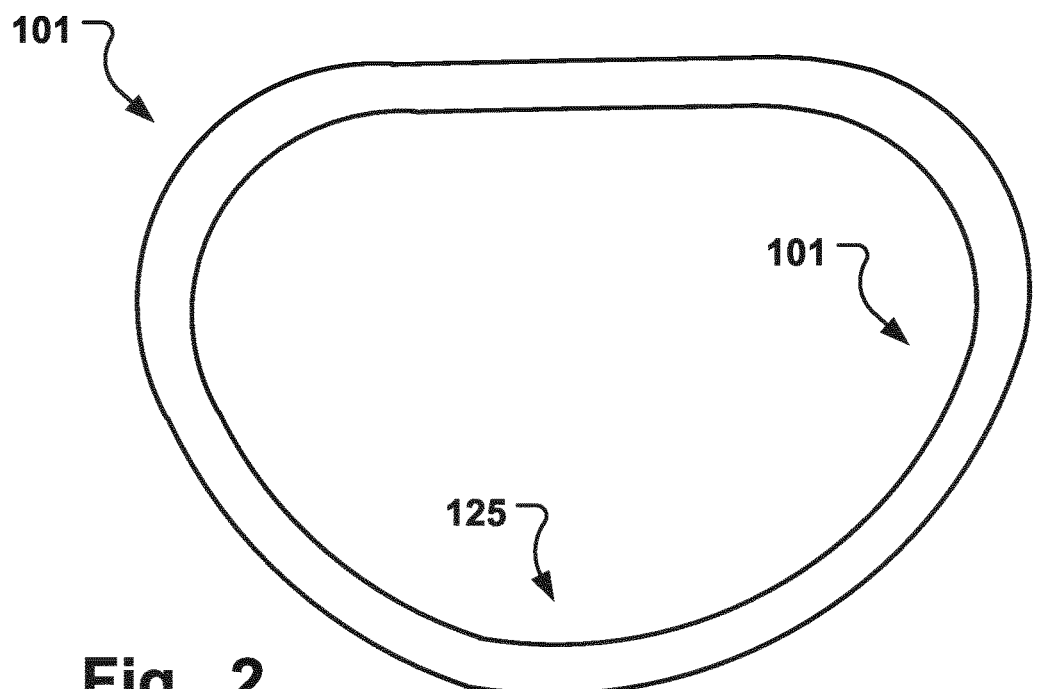
FIG. 2 is an illustration of a cardiac valve implant to be positioned with a medical device according to embodiments of the invention.
Figure 7:
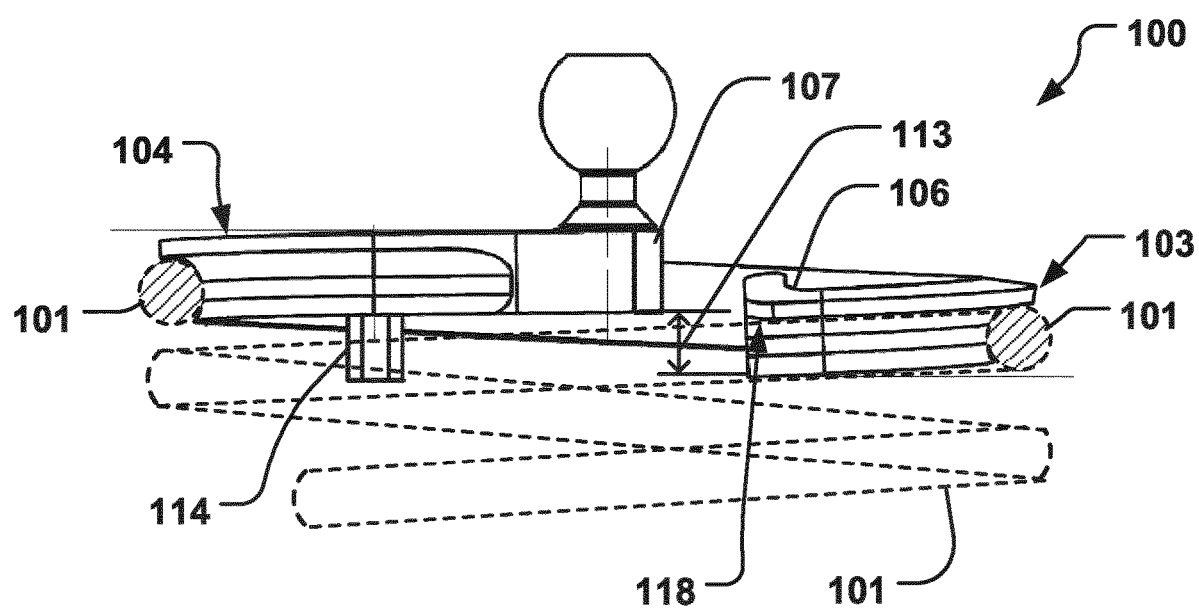
FIG. 7 is a side view of a medical device according to an embodiment of the invention when holding a cardiac valve implant according to FIG. 6 in place.

FIGS. 1*a-b* show a medical device 100 according to an embodiment of the invention, for holding an annuloplasty implant 101 (see e.g. FIG. 2 and FIG. 7). The below description of the medical device 100 according to the embodiment as seen in FIGS. 1*a-b* also applies to the embodiments of the medical device 1300, 1400, 1500, 1600, 1700, 1800, 1900, 2000, 2100, as seen in FIGS. 13-21. The device 100 comprises an elongate support 102 defining a peripheral edge 103 with a curvature about which the annuloplasty implant 101 can be fitted. The support 102 comprises a resilient portion 104 for resiliently holding the annuloplasty implant 101 in place in the medical device 100. The medical device 100 functions as a holder for the implant, and by having a resilient portion 104 the implant 101 can be held in place without the need for any specialized means for attachment, such as sutures and/or the use of holders with several components that are required to hold the implant. Easy attachment and detachment of the implant 101 to the device 101 is thereby achieved, in a less time-consuming manner compared to e.g. using sutures. As the implant 101 has been positioned at a target site, e.g. to resize the annulus of a heart valve, repositioning can be achieved readily by again attaching the implant to the device due to the resilient portion 104, again without the need of a special attachment means. Repeated repositioning is possible in this manner, during a narrow time frame during surgery, due to the quick attachment and detachment possible. The resilient portion 104 is for radially resiliently holding the implant 101 in place in the medical device 100, and/or axially resiliently holding the implant 101 in place in the medical device 100. Radially resiliently holding of the implant 101 is to be construed as the resilient portion 104 is resilient in the radial direction, which direction extends parallel to an axis from the center of the device 100 towards the peripheral edge 103, and thereby providing a force in the radial direction, either radially outwards from the center or radially inwards from the center, for holding the implant 101. The center of the device 100 may be construed as its center of mass, or geometrical center. The radial direction may also be construed as extending along an axis aligned from the position of the control member 110 to the peripheral edge 103. The implant 101 is held in place against the device 100 by the frictional force created in the contact area between the implant 101 and the device 100, e.g. at the peripheral edge 103, which source from the radially directed force applied through the resilient portion 104.

Figure 3:
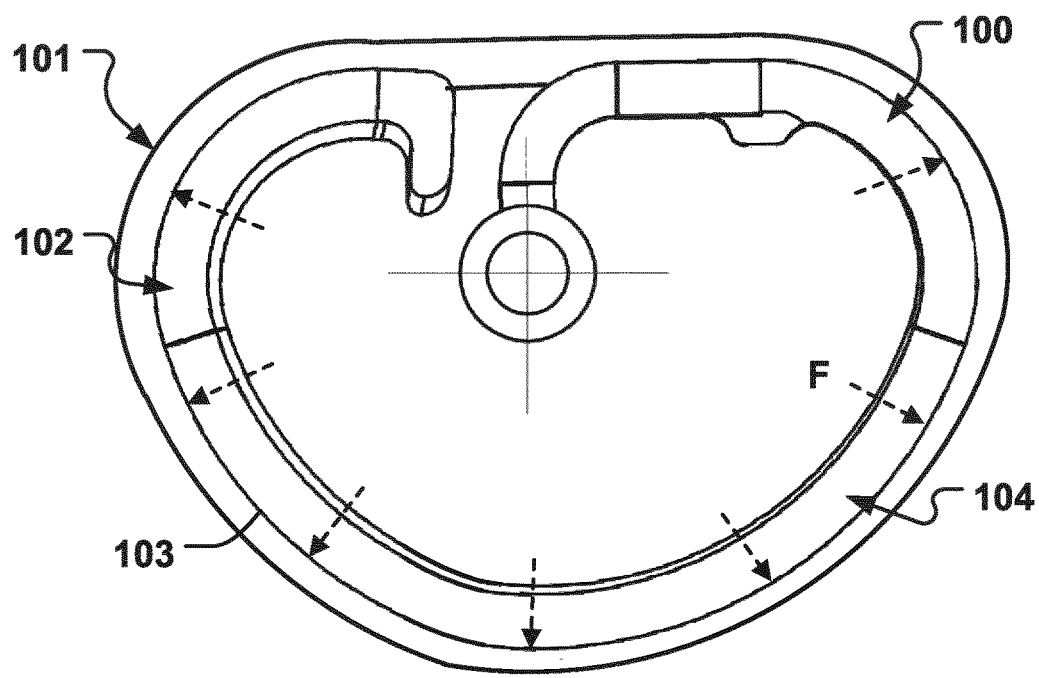
FIG. 3 is an illustration of a cardiac valve implant held in place for positioning with a medical device according to embodiments of the invention.

FIG. 2 shows an annuloplasty ring 101 as an example of an annuloplasty implant 101. In FIG. 3 the elongate support 102 is resilient itself and the resilient portion 104 extends therefore along the peripheral edge 103. The resilient portion 104 holds the implant 101 by applying the radial force (F) along the peripheral edge 103. The force (F) is here applied radially outwards.

Axially resiliently holding of the implant 101 is to be construed as the resilient portion 104 is resilient in the axial direction, which direction extends substantially perpendicular to the radial direction, i.e. the vertical direction in e.g. FIG. 7 showing a side view of the device 100 in FIGS. 1*a-b*. By being resilient in the axial direction the resilient portion 104 may exert a force in the axial direction onto the implant 101 that holds the implant 101 in place. As discussed further below with reference to FIG. 7 the geometry of the implant may in this manner be changed by the applied force from the resilient portion 104 for facilitating insertion of the implant.

Returning to FIGS. 1*a-b*, the support 104 has an expanded circumference (C) in a first configuration (FIG. 1*a*), and a reduced circumference (C') in a second configuration (FIG. 1*b*). The circumference is to be construed in its usual meaning, as the dimension of the device 100 around the peripheral edge 103. When the elongate support is discontinuous, e.g. with two free ends as illustrated in FIGS. 1*a-b*, the circumference is measured as the shortest distance between the free ends at the periphery, as indicated by the dashed line (C, C'). Radial movement of the support 102 between the second and first configuration cause the curvature of the peripheral edge 103 to conform at least partly to the annuloplasty implant 101 to hold the annuloplasty implant 101 in place. The radial movement is due to the resilience of the resilient portion 104. Radial movement between the second and first configuration is to be construed as movement from second to first configuration, or movement from first to second configuration, i.e. radially outward and radially inward. The elongate support 102 may therefore apply a force to the implant 101 in both radially outward and radially inward directions to hold the implant in place. A self-holding action is thereby provided which allows easy removal of the implant from the device 100 and re-insertion if desired. By having an elongate support that is self-holding the disadvantageous prior art solutions with several components for holding the implant are avoided, and no sutures are needed.

The first configuration of expanded circumference (C) may be the relaxed configuration of the device 100, and the second configuration of reduced circumference may be the compressed configuration of the device 100. The resilient portion 104 is unloaded in the relaxed configuration and is loaded, i.e. being tensioned, in the compressed configuration. Hence, as was illustrated in FIG. 3, the radial movement is radial expansion from the second configuration to the first configuration, which causes the curvature of the peripheral edge 103 to conform to the implant 101 and exert a force (F) in the radially outward direction to hold the implant 101 in place. The configuration of the device 100 in FIG. 3 is therefore not the fully expanded circumference, i.e.

not fully relaxed, in order to exert the force (F) on the implant 101. Thus, once the device 100 is put into place in the implant 101, it provides a firm support and the implant 101 and the device 100 can be manipulated without loosing the self-holding contact between the two. An elongate support with a circumference that merely can be changed is not sufficient to solve the aforementioned problems. Previous solutions still rely on having multiple component holder members that must be connected lock the implant in place, and to prevent collapsing of the holder members. The resilient portion 104 of the device 100 being radially expandable between to configurations, as discussed above, avoids such complex mounting systems.

In case of the device 100 apply a radially inward force to the implant (not shown), FIG. 1b illustrates the relaxed configuration, and the resilience of the portion 104 allows expansion of the device 100 to expanded circumference in FIG. 1a. The implant 101 may then conform to the inward edge of the device 100, opposite to peripheral edge 103 to hold it in place.

The resilience of the device 100 in embodiments may be due to the resilient portion 104 being made of a flexible material with shape memory properties, such as a shape memory polymer or metal. Alternatively, the device configurations of expanded and reduced circumference may be achieved by a material of the device 100 having other shape memory properties, such as temperature dependent shapes.

The elongate support 102 may be ring-shaped with at least one central opening 105. As seen in FIG. 1a, the central opening 105 has a substantial area due to the cross-section of the material of the elongate support 102 being substantially smaller than the diameter of the device 100 at any point. This improves the visibility of through the device 100, which is important during the implantation procedure.

In embodiments such as in FIG. 1a the ring-shape is discontinuous so that the elongate support 102 comprises two free ends 106, 107. The free ends 106, 107, allow movement in relation to each other, hence allowing the circumference of the device 100 to be varied to conform to the implant 101. The general shape of the elongate support 102 may be D-shaped, C-shaped, or shaped suitably to allow conforming to the implant 101 while permitting varying of the circumference. In case of not having a discontinuous ring-shape, i.e. a closed ring of any shape, the circumference may be reduced by pulling or compressing the resilient portion 104 inwards and towards the center of the device 100, e.g. as seen in the embodiments in FIGS. 18-19, where first engagement surface 108 may be forced in a direction towards second engagement surface 109. The circumference of the device 100, which would be reduced by said pulling action, should in that case be construed as the shortest path around the periphery, i.e. a circular/oval path without following portions of the edges 103 being pulled towards the center, i.e. extending towards the center. Hence, this would effectively be the cross-section of the device 100, which would decrease by the pulling action. The device 100 may have struts crossing the opening 105 that are arranged so that compressing the struts towards each other the cross-section of the device 100 would be reduced.

As mentioned above, the entire elongate support 102 may be flexible to define the resilient portion 104. This may simplify manufacturing of the device 100, or provide a sufficiently uniform flexibility around the peripheral edge 103 to allow the entire elongate support 102 to conform to the implant 101, as illustrated in FIG. 3, thereby leaving no openings between the edge 103 and the implant 101 for secure attachment. Alternatively, a limited portion of the elongate support may be flexible, and/or the flexibility me be provided by other means such as a spring (not shown) arranged to join two parts of the elongate support 102 together, thereby allowing flexibility between the two parts for varying the circumference of the device 100.

Figure 10:
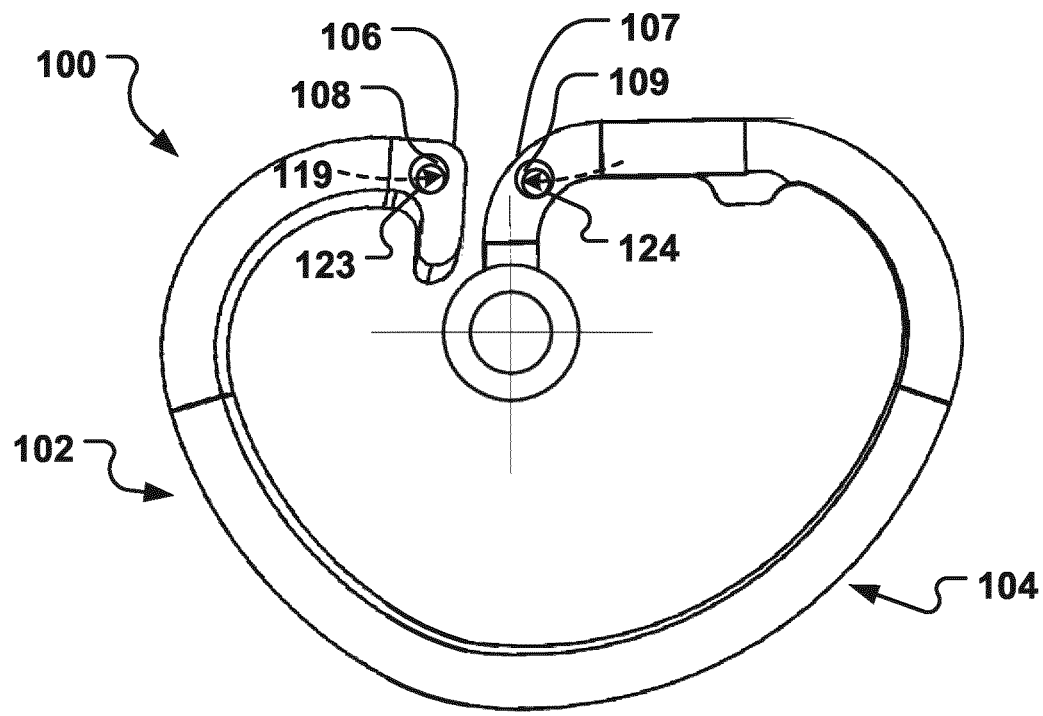
FIG. 10 is an illustration of a medical device according to an embodiment of the invention in a second configuration corresponding to FIG. 1b.

Each of the free ends 106, 107, may comprise an engagement portion 106, 107, having an engagement surface 108, 109, as illustrated in FIG. 1a. The engagement surfaces 108, 109, are adapted to receive a tool for compressing the free ends 106, 107, towards each other in the compressed configuration of the elongate support 102. The direction of compression is indicated for the free ends 106, 107, in FIG. 1b, and is for one end 107 indicated as a first direction 119, and being reversed for the opposite free end 106. Alternatively, if the configuration of reduced circumference (C') would be the relaxed shape, as elucidated above, the free ends may be forced apart by engaging with a tool 200 the surfaces opposite to that of the engagement surfaces 108, 109, for each of the free ends 106, 107. By having engagement surfaces 108, 109, the free ends 106, 107, may be manipulated to achieve the desired shape of the elongate support 102 to be able to conform to the cardiac valve implant 101 and hold it in place. This is an efficient and quick way of manipulating the device 100. Due to the free ends 106, 107, being manipulated directly a compact device 100 is realized. Visibility through the elongate support 102 is optimized due to manipulation at the periphery of the elongate support 102. Alternatively or in addition, the free ends 106, 107, may have apertures 123, 124, with corresponding engagement surfaces 108, 109, for allowing insertion with a tool to manipulate the free ends 106, 107, as illustrated in FIG. 10. It may be advantageous to engage with the tool as close to the elongate support as possible, i.e. either by apertures 123, 124, or by the control member 110, discussed further below, being displaced from the center of the support 102 and positioned close to the peripheral edge 103. Such positioning can improve the ability to position the implant 101 at the target site. Further, improved visibility through the implant 101 is obtained.

The engagement portion 106, 107, and the engagement surface 108, 109, may extend in a radial direction from the peripheral edge 103 of the elongate support 102. In FIGS. 1a-b the engagement surfaces 108, 109, extend radially inwards from the edge 103. A compact device 100 is thereby provided. Alternatively, the engagement surfaces 108, 109, may extend radially outwards from the edge 103. The spatial extent of the engagement surfaces 108, 109, may be optimized for allowing sufficient grip with a tool 200 while visibility is maintained by being confined largely to the periphery of the elongate support 102.

Figures 11A, 11B, 11C:
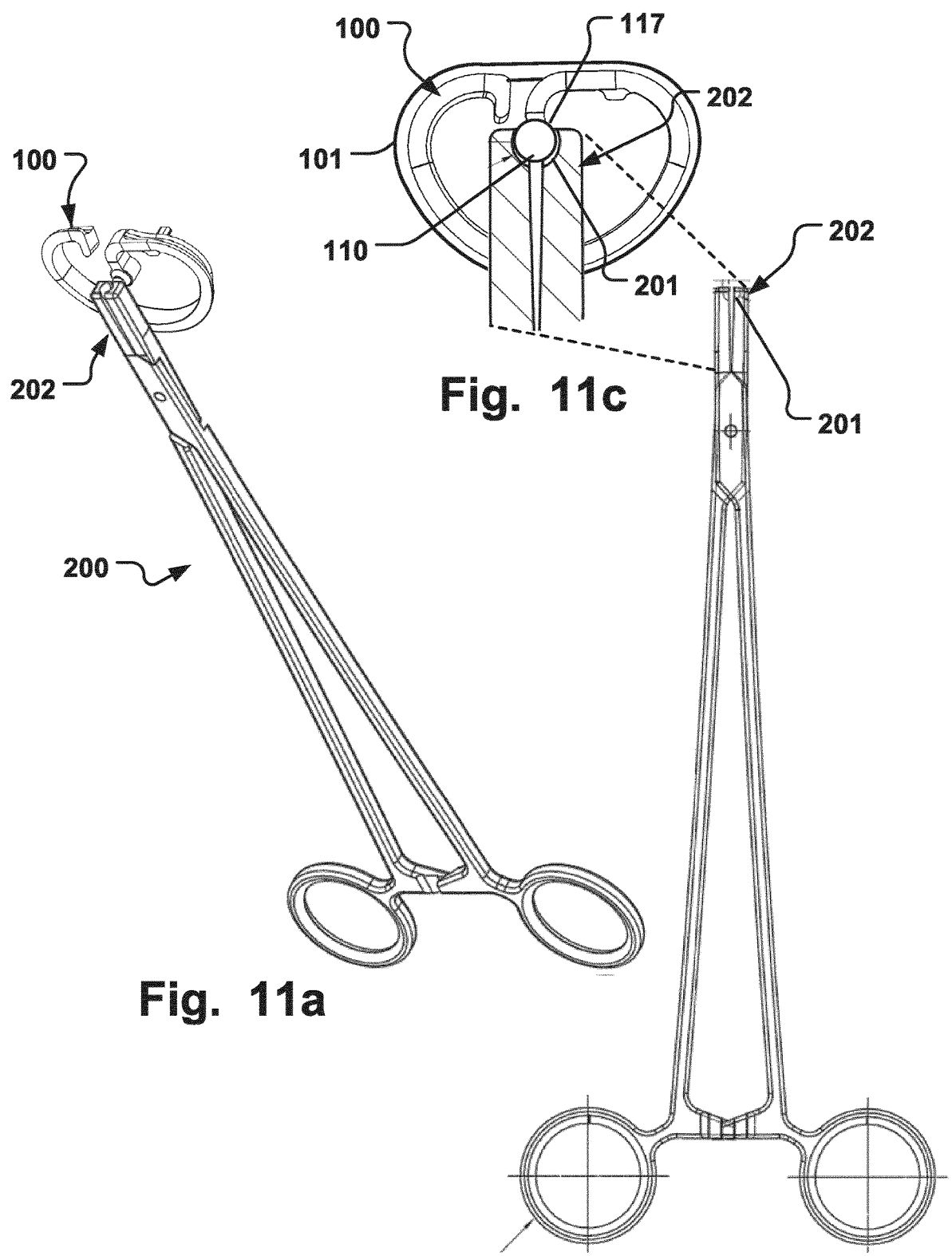
FIGS. 11a-c are illustrations of a tool for holding a medical device according to embodiments of the invention.

The device 100 may comprise a control member 110 for engagement with a positioning tool 200 as seen in FIGS. 11a-c. The control member 110 may comprise a spherical surface 117, as illustrated in the perspective view of the device 100 in FIG. 4. By having a spherical surface 117 the device 100 may pivot in a mating spherical recess 201 of the positioning tool 200. Such pivoting allows the device 100 to be rotated in any desired direction in relation to the positioning tool 200, see e.g. FIG. 11a, which for example allows insertion into the body in a minimally invasive manner, such as through the ribs of the body, and subsequent reorientation when being positioned for implantation at the target site.

The positioning tool 200 in FIGS. 11a-c may be used as a combination instrument. The distal end 202 of the tool 200 is arranged for manipulation of the free ends 106, 107, of the device 100, by contacting the engagement surfaces 108, 109.

Also, the spherical recess 201 mates with the spherical surface 117 for pivotable positioning of the device 100. The spherical recess 201 is illustrated in FIG. 11c which is a magnification of the distal end 202 seen in FIGS. 11a, and 11b. In FIG. 11c the device 100 holding the implant 101 is pivotably held with the tool 200 via control member 110 having the spherical surface 117. Positioning of the device 100 onto the implant 101 and delivering of the implant 101 to the target site is thereby achieved with the same tool 200. Other types of tools having a spherical recess 201 and/or engagement members for the free ends 106, 107, and can be used with the device according to the above.

Figure 6:
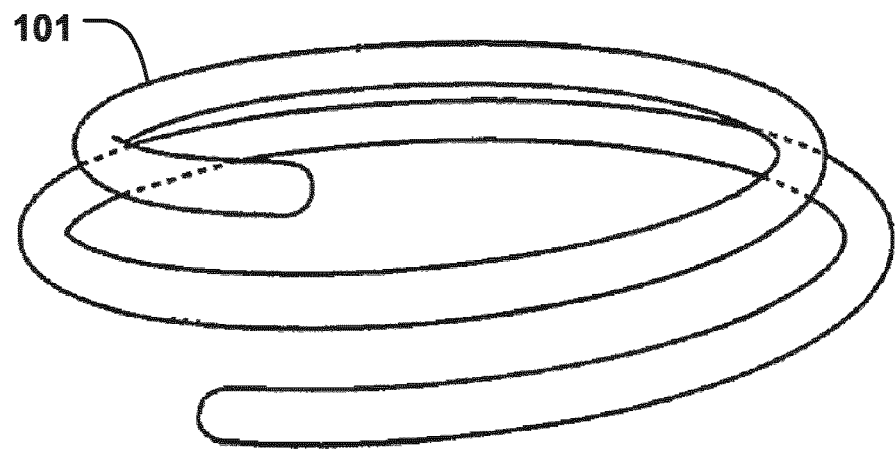
FIG. 6 is an illustration of a cardiac valve implant to be positioned with a medical device according to embodiments of the invention.

The control member 110 may be fixed to one of the free ends 106, 107, off-center from the central opening 105. In FIG. 1a, the control member 110 is fixed to the free end 107, and is positioned slightly above the center of the opening in vertical direction. This may provide increased visibility through the opening 105. At the same time the control member 110 may be positioned slightly towards the center, and alternatively at the center of the device 100, so that rotation of the device 100 around an axis extending through the control member 110, i.e. substantially perpendicular to the plane spanned by the curvature of the elongate support 102, corresponds to a rotation of the device 100 substantially around it central axis without lateral displacement. This may ease the positioning at the target site if the implant 101 is to be turned into position, as in the case of having a helical implant 101 as illustrated in FIG. 6. Further, the device 100 may be used to hold helical downsizing tools, such as disclosed in WO2009/080801.

In FIG. 1a the engagement portions 106, 107, extend radially inwards from the peripheral edge 103, and the control portion 110 is fixed to an end 111 of the engagement portion 107. By having the control member 110 fixed to an end of one of the engagement portions 106, 107, it is easy to switch mode from attaching or detaching the device 100 to/from the implant 101 by engaging the contact surfaces 108, 109, and to engaging the control member 110 for moving the device 100 to or from the target site. The switch can be made in one fluent motion, by using the combination tool 200, and reduces the time of the procedure and generally provides an increased degree of control. As mentioned above, the device 100 can be made compact in this manner, e.g. no additional fixation structures for the control member 110 extending across the opening 105 are necessary, improving visibility.

Figure 5A:
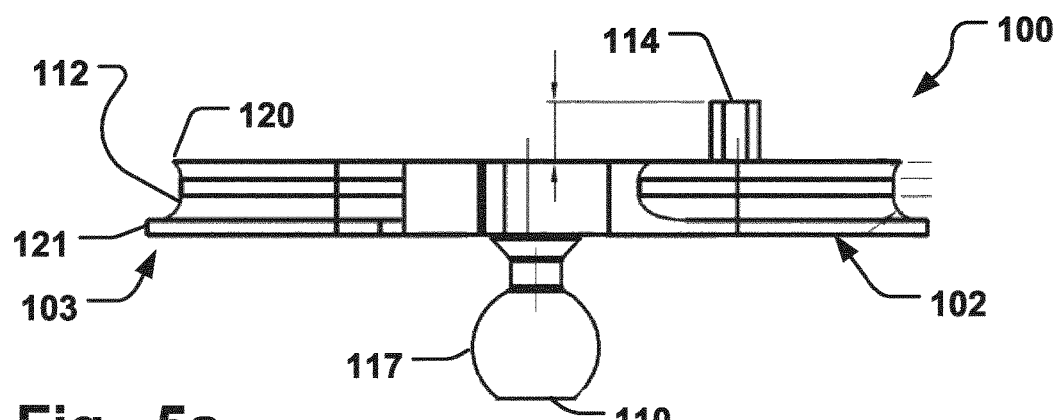
FIGS. 5a-b are side views of a medical device according to an embodiment of the invention, when not holding a cardiac valve implant (a), and when holding a cardiac valve implant in place (b)
Figure 5B:
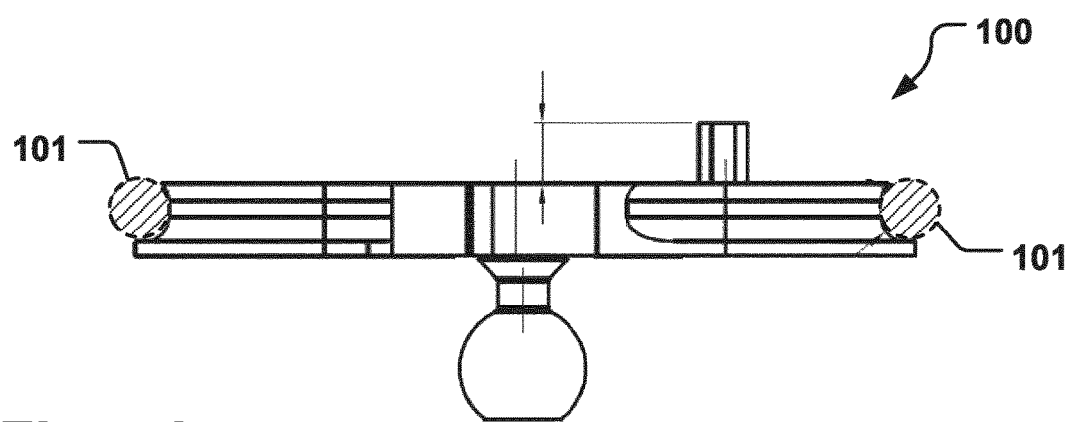

The elongate support 102 may comprise a radially outwardly opening or groove 112 along the peripheral edge 103 dimensioned to receive the annuloplasty implant 101. This is illustrated in FIGS. 5a-b which corresponds to side views of the device 100 in FIGS. 1a-b, with and without holding of the implant 101 in FIGS. 5a and 5b, respectively. The groove 112 provides efficient retaining of the implant 101 by the device 100. The groove 112 may have a curvature similar to that of the implant 101, so that the contact surface between the implant 101 and the device is increased, thereby allowing a further increased retaining force of the implant 101. Upon expansion of the elongate support 102 from the configuration of reduced circumference (C') to the configuration of increased circumference (C) the groove 112 conforms to the implant 101 as seen in FIG. 5b.

The recessed surface of the groove 112 may have other shapes to fit other types of implants, such as triangular, rectangular or oval. The groove 112 has side edges 120, 121, between which the recessed surface of the groove 112 extends. The side edges 120, 121, extend along the groove around the elongate support 102, and may be offset in relation to each other in the radial direction. I.e. in FIG. 5a the first side edge 120 extending on the side of the elongate support 102 opposite to that side of which the control member 110 extends from, i.e. the distal side, has a shorter radial extent than the second side edge 121. This may provide for an easier positioning of the implant 101 into the groove 112, as the circumference of the elongate support 102 at the location of the first side edge 120 at the distal side is smaller than that of the second side edge 121. Hence, less compression of the resilient member 104 of the elongate support 102 becomes necessary for the curvature to conform to the implant 101, when inserted from the distal side.

Figure 4:
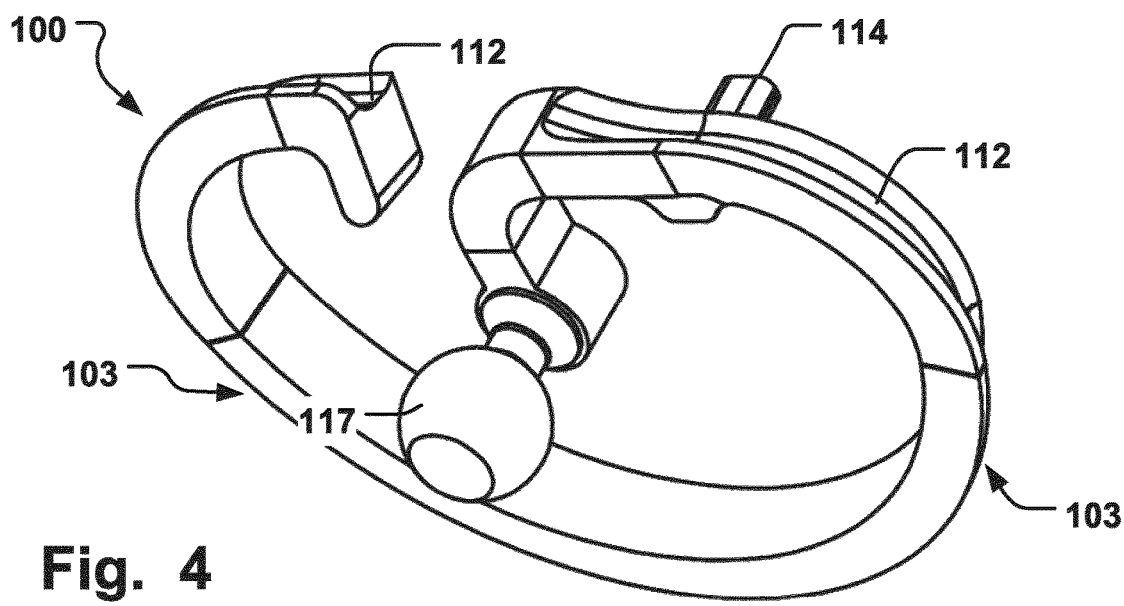
FIG. 4 is a perspective view of a medical device according to an embodiment of the invention.
Figure 9:
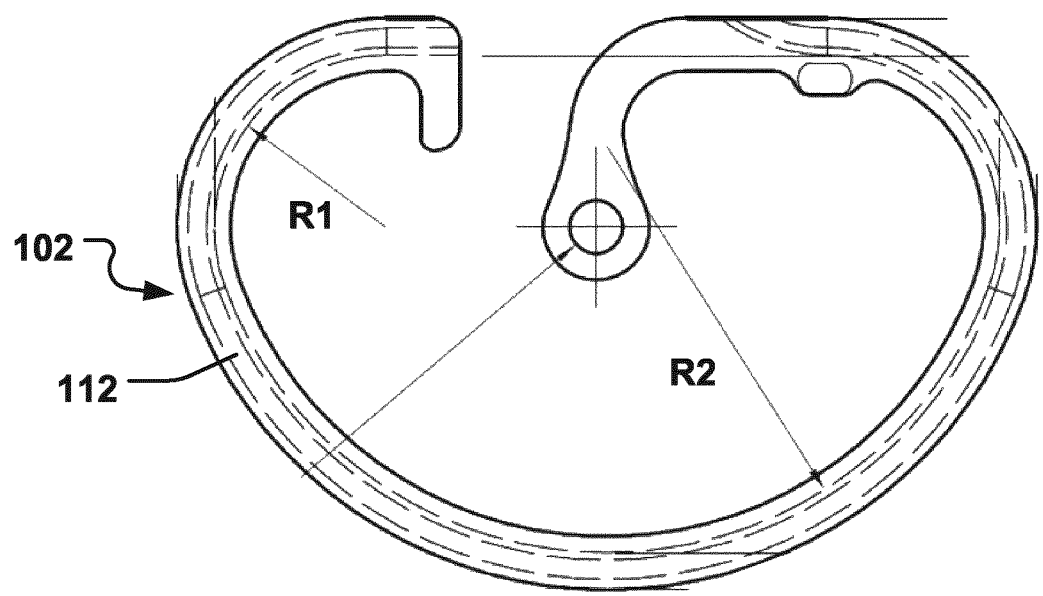
FIG. 9 is an illustration of a medical device according to an embodiment of the invention.

FIG. 4 shows a perspective view of the device 100. The groove 112 extends around the elongate member 102, which is shown in further detail in FIG. 9, which is a top down view, similar to that in FIGS. 1a-b, of the device 100. Also indicated in FIG. 9 is the different radius of curvature (R1, R2) of the elongate support 102. As mentioned above, the shape of the elongate support may vary, and the radius of curvature may vary along the elongate support 102.

The curvature of the peripheral edge 103 of the elongate support 102 may generally follow a three-dimensional path 118 such that the curvature conforms to an annuloplasty implant 101 extending in a corresponding three-dimensional path. Various implants 101 having different shapes can thereby be held in place by the device 100. An example is illustrated in FIG. 7, where the peripheral edge 103 follows the path 118 of the implant 101, seen in FIG. 6, which is marked by dashed lines. Here the discontinuous ring-shape of the elongate support 102 generally follows a three-dimensional path 118 such that the free ends 106, 107, are axially off-set 113. The off-set 113 is in the axial direction which is substantially perpendicular to the plane spanned by the elongate support 102 in the radial direction. The off-set 118 is such that the curvature of peripheral edge 103 follows the helix-shaped implant 101. The off-set 113 may be adjusted to fit the helix-shaped implant 101 if the distance between adjacent turns of the helix is varied. Alternatively the free ends 106, 107, way be aligned without off-set 113, but the peripheral edge 103 at other parts of the elongate member 102 may follow a curvature or path 118 in the axial direction, e.g. at a mid-section of the elongate support 102 between the free ends 106, 107. For example, implants 101 may have the posterior side 125, as indicated in FIG. 2, elevated in the axial direction from the other parts of the implant 101, and the elongate member 102 may be elevated at the corresponding portion to conform to the entire curvature of the implant 101. Other implants 101 may be saddle-shaped, i.e. convex or concave, or be asymmetrical in various configurations, whereby the elongate member 102 has the corresponding saddle shape or asymmetry.

The spatial extent of the path 118 may also provide for modifying the geometry of the implant 101. For example, the off-set 113 may be increased to force the rings of a helical implant 101, in FIG. 6, apart when the implant 101 is held in place by the device 100. This may facilitate insertion of the implant 100 through the annulus at the target site, as friction against the tissue may be reduced. When the device 100 is removed from the implant 101, the helical rings may assume their unstrained condition. By being resilient in the axial direction the resilient portion 104, which may be defined by the entire elongate support 102 being resilient, the geometry of the implant 101 may be modified by first compressing the device 100 in the axial direction and fit it to the implant 101, and then let the device 100 relax, whereby the implant 101, in this case being flexible, follows the expansion of the device 101. The groove 112 provides for locking the implant 101 in place and thereby forcing the rings of the implant 101 to follow the path 118 of the elongate support 102 when the elongate support 102 assumes its relaxed configuration.

The elongate support 102 may comprise a retainer pin 114 extending axially in a direction substantially perpendicular to a plane spanned by the curvature of the peripheral edge 103, as illustrated in FIGS. 4 and 5a. The retainer pin 114 is arranged to exert a radial force on the annuloplasty implant 101 to stop radial movement of the annuloplasty implant 101 when held in place by the device 100. The implant 101 is thereby prevented from slipping off the device 100, as radial movement is prevented by the pin 114. In particular, when the device 100 and the implant 101 is rotated, the force exerted on the implant 101 by surrounding tissue may cause a displacement in the radial direction, which now is prevented by the pin 14. A safer procedure and an improved grip of the implant is therefore achieved. As seen in FIG. 7, the retainer pin 114 extends from the distal side of the elongate support, i.e. in relation to the control member 110, and is placed such that it is in abutment with the implant 101, i.e. one of the helical rings of the implant 101. The position of the retainer pin 114 is seen also in the perspective view in FIG. 4, however it may be positioned at any part of the elongate support 102 provided it prevents radial movement of the implant 101.

Figure 8A:
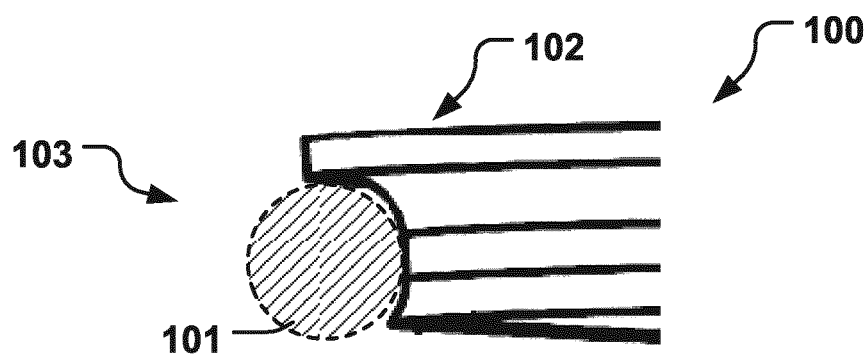
FIGS. 8a-c are side views of a detail a medical device according to embodiments of the invention when holding a cardiac valve implant in place.
Figure 8B:
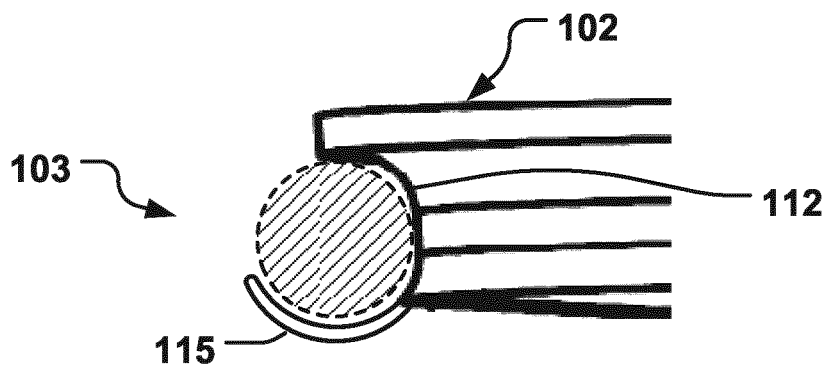

The elongate support 102 may comprise a friction reducing sheath 115 along the peripheral edge 103 which extends in a radial direction to cover a portion of the annuloplasty implant 101 when held in place by the device 100. By covering a part of the implant 101 when held in position by the sheath the friction is reduced between the implant 101 and the surrounding tissue. This allows the implant 101 to be more easily positioned without getting stuck on the tissue, for example when rotating the implant 101 into place at a target site such as through the leaflets of a valve. FIG. 8a shows a detail part of the elongate support 102 at the peripheral edge 103 with the implant held in place at the edge 103. FIG. 8b illustrates the friction reducing sheath 115 extending in the radial direction and covering a part of the implant 101. The sheath 115 may extend along the entire edge 103 of the elongate support 102. The sheath 115 will now prevent the tissue from contacting part of the implant 101. The amount of coverage of the implant 101 by the sheath 115 may be varied by increasing or decreasing the length of the sheath 115. More coverage may be suitable in some applications where low friction is particularly required. The sheath 115 may conform to the curvature of the cross-section of the implant 101, or may have other shapes to provide protection from tissue while allowing sufficient ease of insert of the device 100 to the implant 101. The sheath may be made of any material such as a polymer or a metal alloy providing low friction.

Figure 8C:
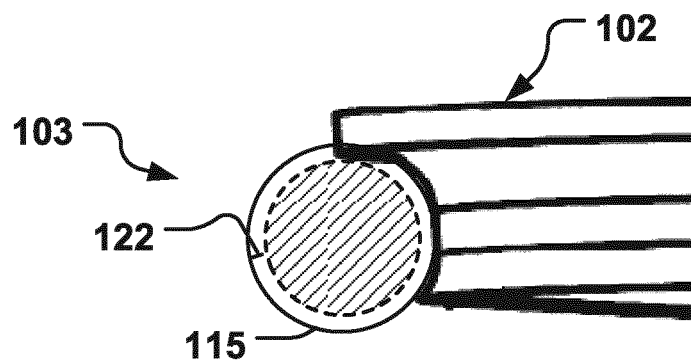

FIG. 8c shows an alternative configuration of the friction reducing sheath 115, covering the entire implant 101. The sheath 115 may be applied to the implant 101 before engaging with the device 100 and then, after being engaged and held in place by the device 100, removed when the implant 101 has been positioned at the target site. The sheath 115 may have an opening or discontinuity 122 which allows easy removal. In FIG. 8c, the sheath 115 may be fixated into the device 100 after the implant 101 is engaged with the edge 103, for example by a weld or glue portion between the sheath and the elongate member 102. When the implant 101 is inserted at the target site and the device 100 is removed, the sheath 115 will disengage from the implant 101 and be retracted together with the device 100. The opening or discontinuity 122 may allow for such disengagement.

The device 100 may comprise an indicator mark 116 being positioned at a first side of the elongate member 102 to mark a geometric feature of the implant 101 on a second opposite side of the elongate member 102, which may not be visible when the implant 101 is held in place at a target site. This allows easier maneuvering e.g. when an end of a helical implant 101, shown in FIG. 6, must be positioned at an opening of the annulus, but being obscured by the elongate support 102. Such indicator 116 is shown in FIG. 1a, and may be positioned anywhere on the device to facilitate the implantation procedure. Indicator marks may also be placed to mark anatomical features, such as the commissures. The indicator mark 116 may be made of a material visible in X-ray. The device 100 may have other indicators visible in X-ray or other imaging techniques, or the device 100 may be made in part or entirely of such material. The device 100 may have a channel or void containing a gas such as air as an indicator. Such indicators allow determination of the position and orientation of the device 100 in the body.

Figure 12:
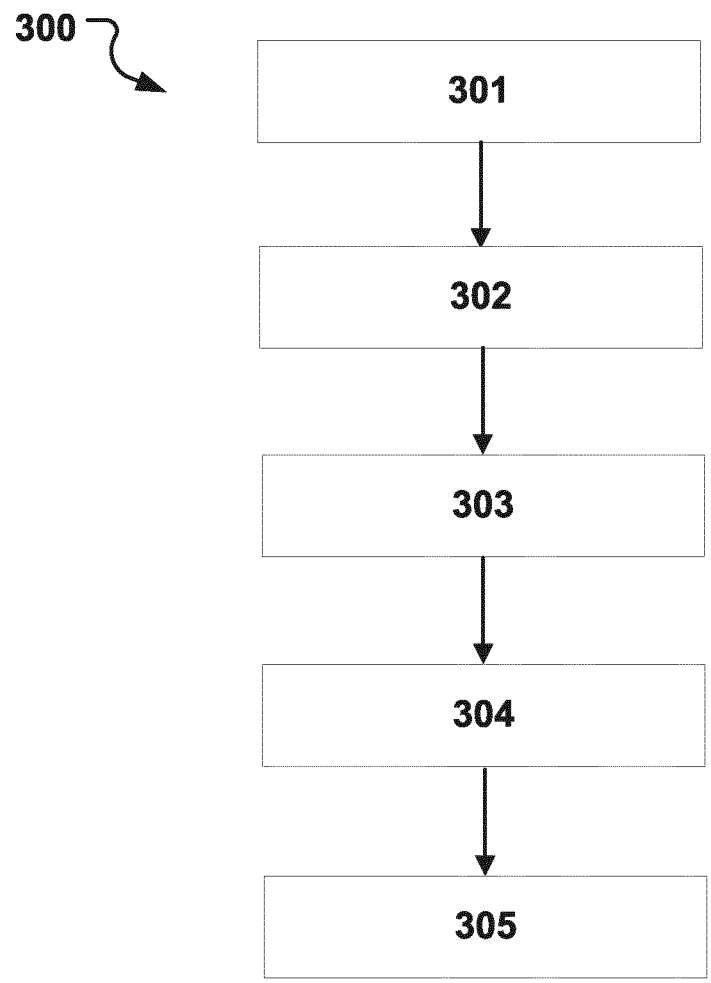
FIG. 12 is a flow chart illustrating a method of positioning a cardiac valve implant with a medical device according to embodiments of the invention.

FIG. 12 shows a flow diagram of a method 300 of positioning an annuloplasty implant 101 at a target site at an annulus with a medical device 100 having an elongate support 102 comprising a resilient portion 104. The method 300 comprises resiliently holding 301 the annuloplasty implant 101 in place in the device 100, positioning 303 the implant 101 at the target site, and loading 305 the resilient portion 104 for releasing the annuloplasty implant 101 from the device 100.

Resiliently holding the annuloplasty implant 101 may comprise loading 302 the resilient portion 104 for transforming the elongate support 102 from a first configuration to a second configuration, whereby radial movement of the elongate support 102 between the second and first configuration cause resiliently holding the annuloplasty implant 101 in place in the device 100.

Positioning the device 100 may comprise pivoting 304 the device 100 having a spherical surface 117 in a spherical recess 201 of a tool 200 for insertion into a body in a minimally invasive manner. The pivoting allows the device while held in place by the tool 200 to adapt to various anatomies to reach the target site. The pivoting 304 may comprise positioning the device 100 such that a plane spanned by the elongate support is substantially parallel to a longitudinal axis of the tool 200 for minimally invasive insertion. This is illustrated in FIG. 11a, where the device 100 is parallel to the longitudinal direction of the tool 200. This allows for example for insertion trough the ribs of a body.

Holder with Improved Grip Section

Figure 13A:
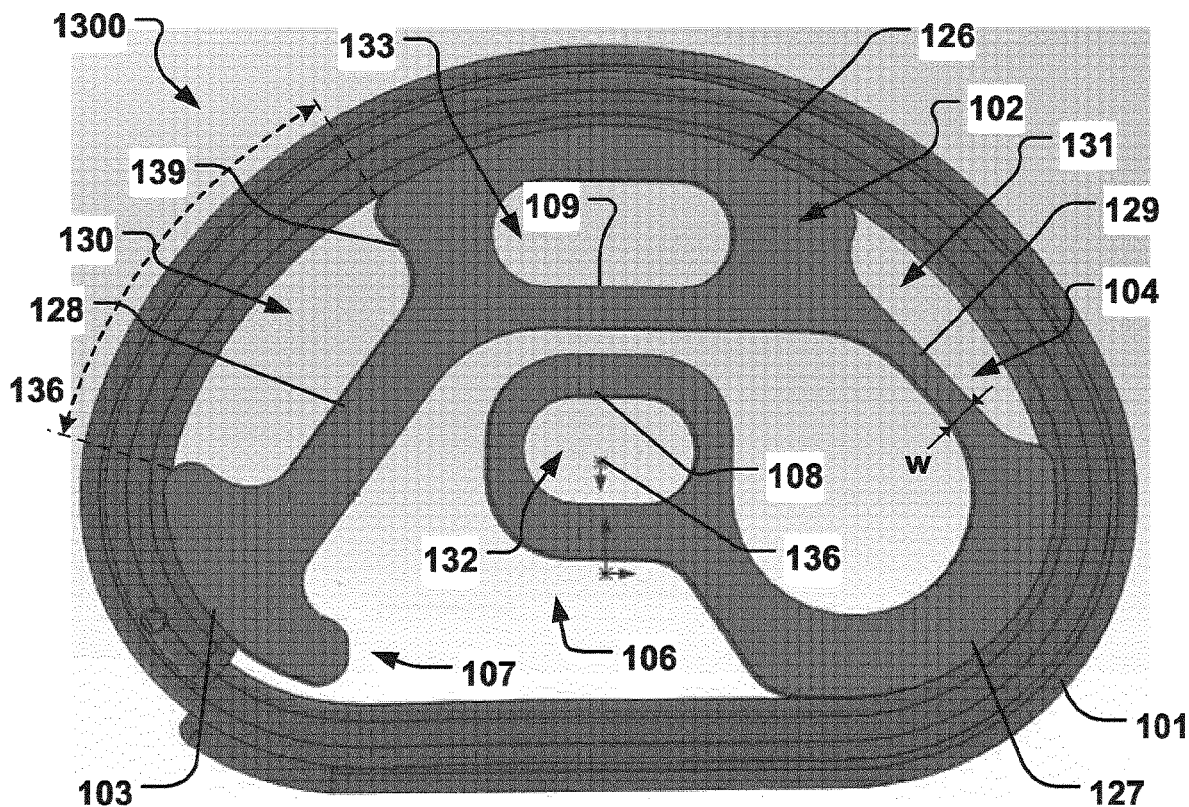
FIGS. 13a-b are illustrations of a medical device according to an embodiment of the invention holding a cardiac valve implant in place, where (a) is a top-down view and (b) is a perspective view.
Figure 13B:
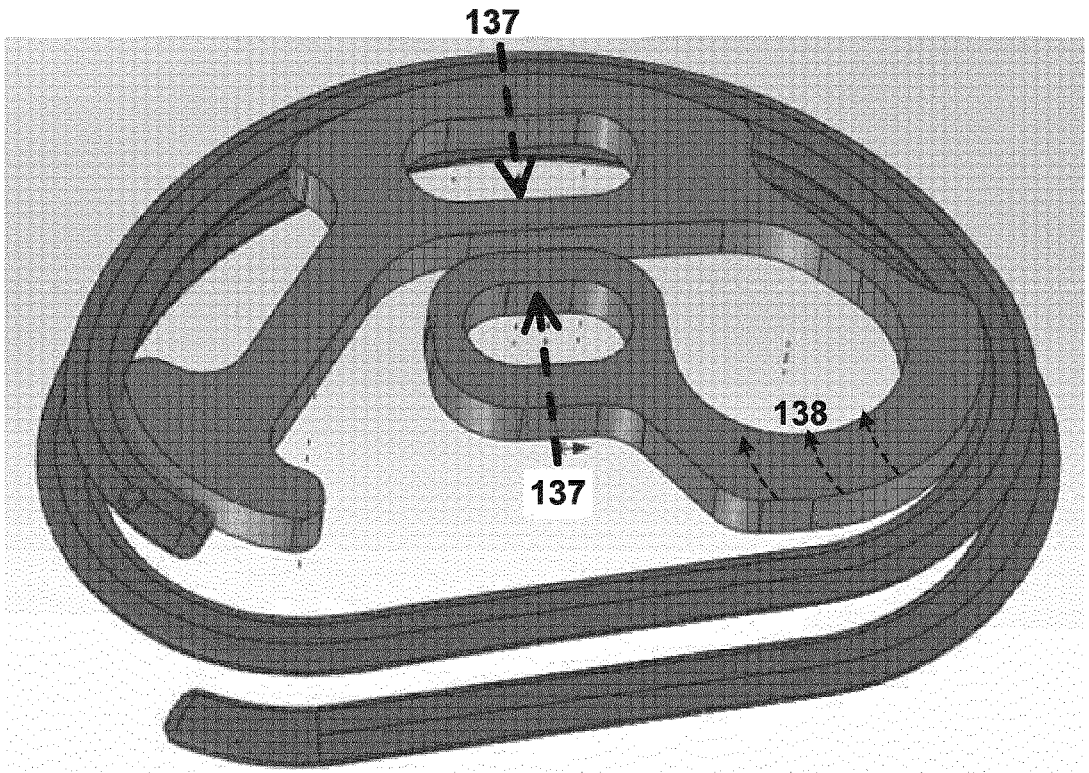
Figure 14A:
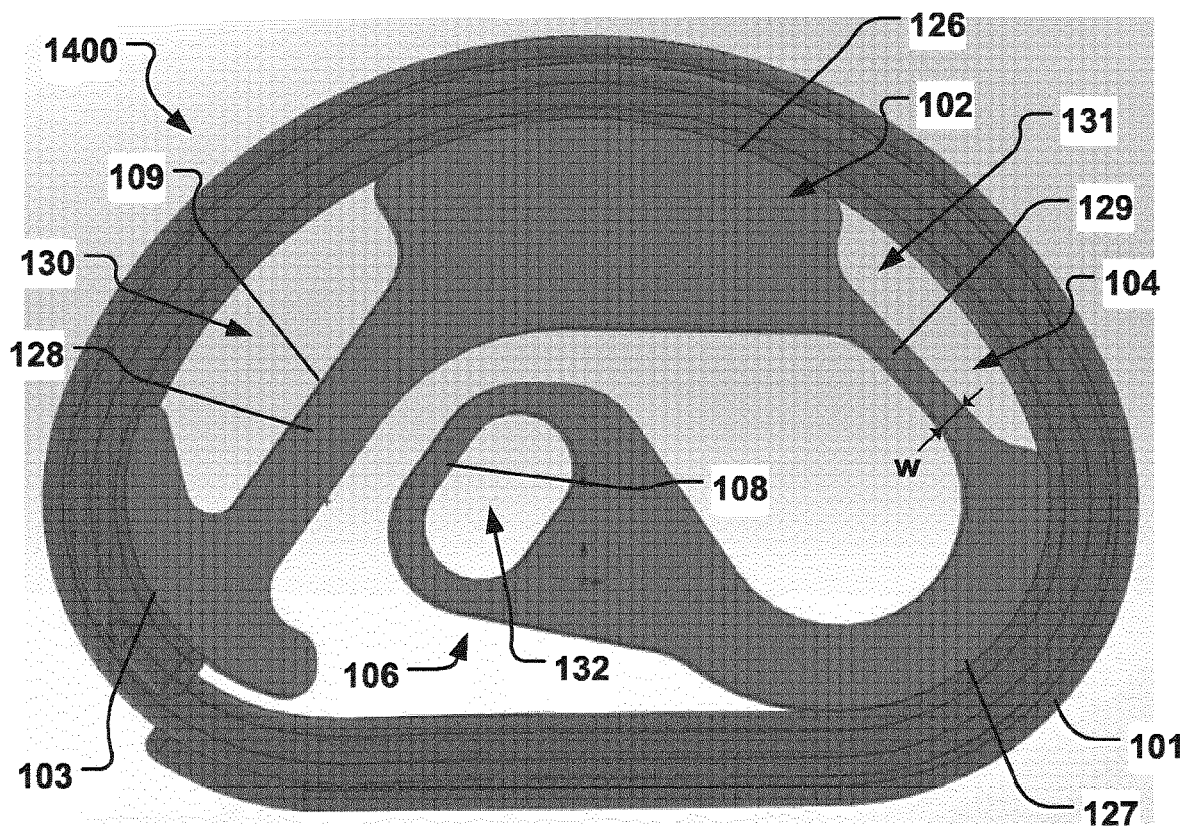
FIGS. 14a-b are illustrations of a medical device according to an embodiment of the invention holding a cardiac valve implant in place, where (a) is a top-down view and (b) is a perspective view.
Figure 14B:
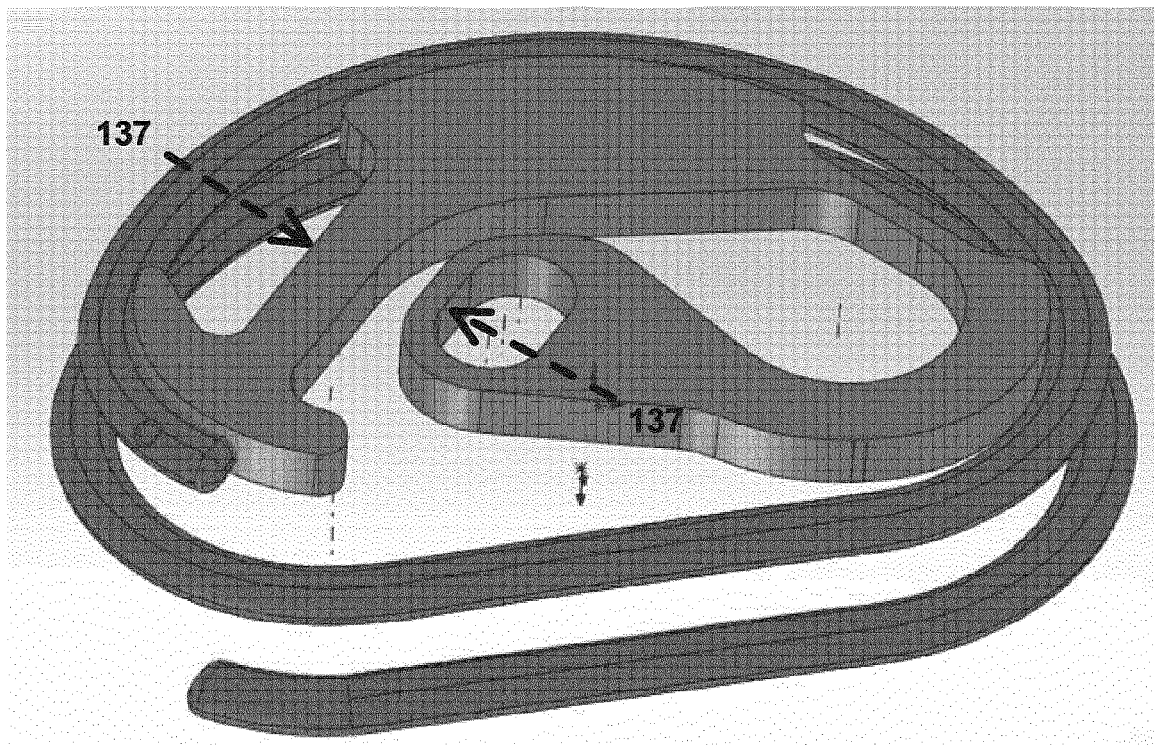

FIGS. 13a-b, illustrates a medical device 1300 according to another embodiment of the invention for holding a cardiac valve implant 101. The device 1300 comprises a support 102 defining first and second peripheral edges 103, 126, respectively, each with a curvature about which the cardiac valve implant can be fitted. The support 102 further comprises a grip section 128 positioned between and connected with the first and second peripheral edges 103, 126, at opposite sides of the grip section 128, in a manner such that the grip section 128 defines an opening 130 for engagement with a gripper tool 400 in use of the support 102. The holder 1300 thereby allows easy manipulation, e.g. by gripping the grip section 128 at any time during the procedure and applying twisting or pushing/pulling action on the grip section. At the same time, the device 1300 maintains a compact shape and visibility is provided through the opening 130 at the periphery during the procedure of positioning the implant 101. The opening 130 separates the first and second peripheral edges 103, 126. The grip section 128 may be directly connected at its opposite ends to the first and second peripheral edges 103, 126. This allows for a compact holder and a minimum of structural elements to interfere with the view through the holder, while means for manipulation in all directions, such as along several points close to the periphery, is improved. The support 102 may further comprise a resilient portion 104 for resiliently holding the cardiac valve implant 101 in place in the device 1300. The support 102 may function as described above in relation to any of FIGS. 1-12. The shape of the support 102 can be changed, due to resilient properties, to provide a temporary hold of the implant 101. For example, with respect to FIG. 1b, a force as indicated by arrows 137 may be applied on engagement surfaces 108, 109, respectively, to compress the support 102 which bends in direction of arrows 138 in order to assume a reduced circumference for positioning inside the implant 101. Once the force is released the support assumes the relaxed expanded configuration where first and second peripheral edges 103, 126, and further a third peripheral edge 127 may conform to the curvature of the implant 101 to hold it in place. The grip section 128 positioned between first and second peripheral edges 103, 126, allows the support 102 to freely conform to the implant 101 while providing an integral means for manipulating the support, and thereby the implant, thereby dispensing with the need for separate manipulation means.

FIG. 13a illustrates an embodiment that the grip section 126 is recessed radially inwards from the first and second peripheral edges thereby defining the opening 130 between the support 102 and the cardiac valve implant 101, when the latter is held in place by the support. Hence, there is an open void from the grip section 128 radially outwards towards the implant 101, and the borders defining the opening 130 is given by the implant and the grip section, and walls 139 that join the peripheral edges 103, 126, with the grip section. The recess, i.e. opening 130, which is created by the recessed grip section 128 may have different shapes. For example, the recess or opening 130 may have any elongate shape. This allows manipulation of the support 102 close to its periphery while at the same time allowing good visibility at the periphery. Manipulation close to the periphery with a gripper tool may improve the degree of control during certain stages of the implant insertion procedure. This also allows a compact device, e.g. minimizing the amount of material, that ease manufacturing and also ease control of e.g. shape-changing properties of the support, such as obtaining the required spring force constants for setting the proper resilience properties of the support 102. Also, as the grip section 128 join the first and second peripheral edges 103, 126, in this manner, with an opening 130 that shifts the periphery of the support 102 radially inwards, the bending radius of the support can be more freely chosen with respect to a D-shaped support by varying the position and shape of the grip section 128, as the grip section may define the periphery, i.e. outer border, of the support 102 between the first and second peripheral edges 103, 126. This in turn may allow particular customization of the dynamics of fitting the implant 101 to the support 102, such as easier to snap in the support 102 place and also remove from the implant. The grip section 128 may comprise an elongate portion that extends at least partly along the longitudinal direction of a portion of the implant that extends between said first and second peripheral edges, when held in place by said support. For example, as seen in FIG. 13a, grip section 128 follows generally the direction of the implant along portion 136 that extends between said first and second peripheral edges, i.e. the portion radially outside opening 130.

As illustrated in FIGS. 13a-b, the support 102 may comprise a third peripheral edge 127 with a curvature about which said cardiac valve implant can be fitted, and where the third peripheral edge 127 is connected to either of the first and second peripheral edges 103, 126, by a second grip section 129. In FIGS. 13a-b, the third peripheral edge 127 is connected to the second peripheral edge 126. This allows a second position for engagement with a grip tool during a procedure, with the same advantages as described above in relation to the first grip section 126.

The grip section 126 may be elongate as seen in FIGS. 13a-b, and positioned off-center from a center point 135 of the support 102 and at a distance from the implant 101, when held in place by the support, where that distance corresponds substantially to the width of the opening 130. The grip section 126 may extend substantially parallel to a portion 136 of the implant 101, which portion defines the border of the opening 130 together with the grip section. The same may apply to the second grip section 129 and opening 131, as seen in FIGS. 13a-b. The shape of the grip section 126, 129, and the angle relative to the implant 101, when held in place by the support 102, may be optimized for engagement with a particular grip tool.

As described in relation to device 100, the support 102 may have an expanded circumference (C) in a first configuration, and a reduced circumference (C') in a second configuration, wherein radial movement of the support 102 between the second and first configuration cause the curvature to conform at least partly to the cardiac valve implant 101 to hold the cardiac valve implant in place, and wherein the first configuration is relaxed and the second configuration is compressed, and the radial movement is radial expansion from the second configuration to the first configuration.

As illustrated in FIGS. 13a-b, the medical device 1300 may comprise a first engagement surface 108 adapted to receive a tool 200 for compressing the first engagement surface 108 towards an opposite second engagement surface 109 of the support 101 in a compressed second configuration. Also as illustrated in FIGS. 13a-b, the support may comprise two free ends 106, 107, where one of the free ends, such as a first end 106 comprises the first engagement surface 108. Here, the second engagement surface 109 is provided between the first and third peripheral edges 103, 127. At least one of the first and second engagements surfaces may be defined by the inside surface of an engagement aperture 132, 133. This may allow for a more easy, safe and controllable positioning with an engagement tool at the support 102.

The grip section 128, 129, may be flexible to define the resilient portion of the medical device 1300-1900. Portions of the support 102 may be made differently resilient in order to optimize the function of the device 1300-1900 as a temporary holder for the implant 101. For example, the portions defining the peripheral edges 103, 126, 127, may be more rigid than the grip sections 128, 129, to define a solid contact with the implant 101, which may be provided by having either of the grip sections 128, 129, of a smaller cross-section than the aforementioned portions 103, 126, 127. Substantially the entire support may be flexible to define the resilient portion of the medical device 1300-1900, as previously described with reference to device 100.

Figure 23:
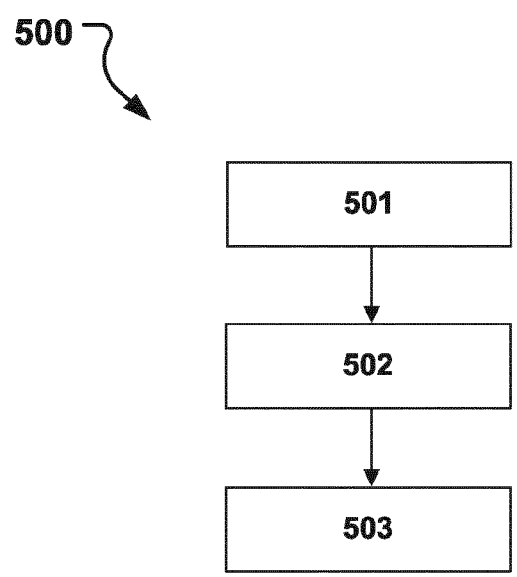
FIG. 23 is a flow chart illustrating a method of manufacturing a medical device according to an embodiment of the invention.

The width (W) of the first or second grip sections 128, 129, may be chosen to set a predetermined spring force constant of the support 102, to thereby optimize the response of the support 102 when applying a desired amount of force with an engagement tool at the engagement surfaces 108, 109. The support 102 may be comprised of a monolithic piece of a polymer material. This allows for easy mass-production, where the entire support can be extracted out of a bulk material, such as a polymer with suitable elasticity module (E), by punching out the support from a sheet of material, by laser or wire sawing, or by molding or extrusion. FIG. 23 illustrates a method of manufacturing 500 a medical device for holding a cardiac valve implant 101, such as a device 1300-2100, and is described in more detail below. The support may also be made from a Titanium alloy.

The medical device 1300-1900 may comprise a locking mechanism 134 (not shown) for fixating the support 102 in a first expanded configuration. This may allow for a more forceful handling of the support 102, without risking that the support is compressed and becomes displaced with respect to the implant 101.

The embodiments illustrated in FIGS. 14-21, of medical device 1400-2100 share generally the same features and advantages as described above. More particularly, FIGS. 14a-b show a device 1400 with a support 102 having an engagement surface 109 at the grip section 128, that can be compressed towards opposite engagement surface 108 at the free end 106 of the support 102.

Figure 15A:
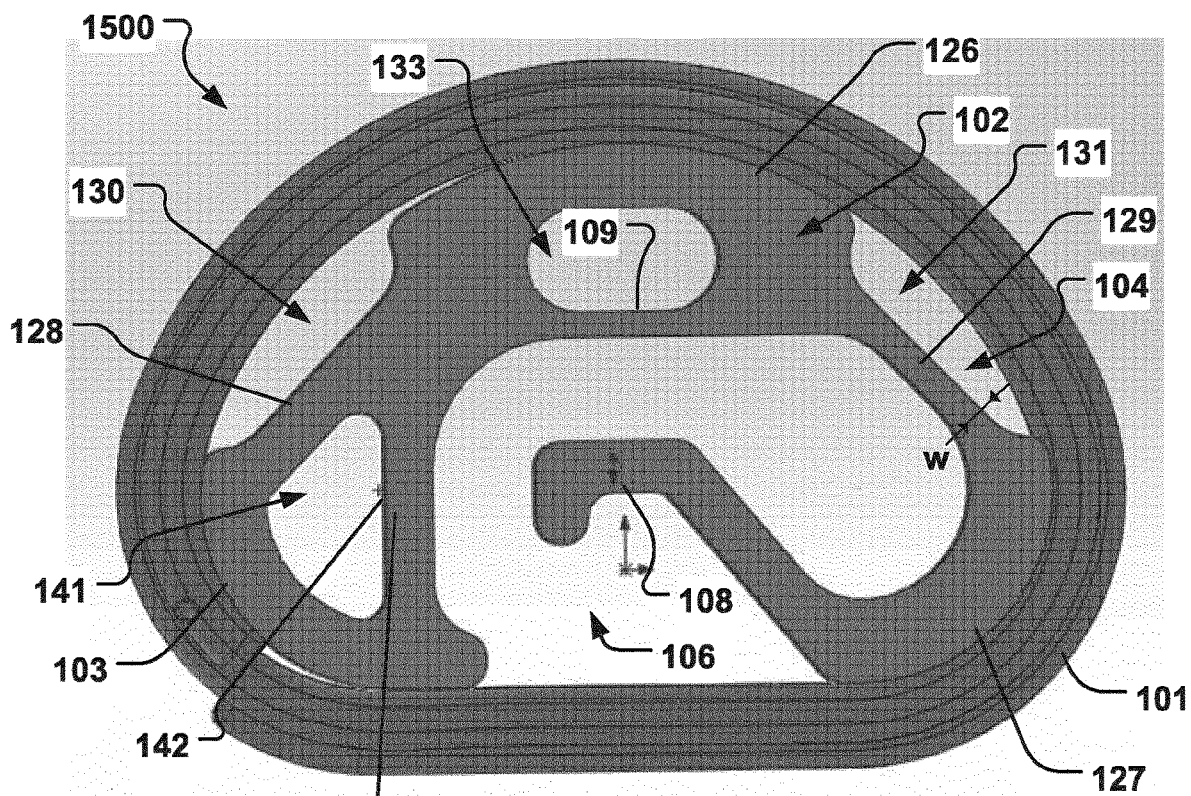
FIGS. 15a-b are illustrations of a medical device according to an embodiment of the invention holding a cardiac valve implant in place, where (a) is a top-down view and (b) is a perspective view.
Figure 15B:
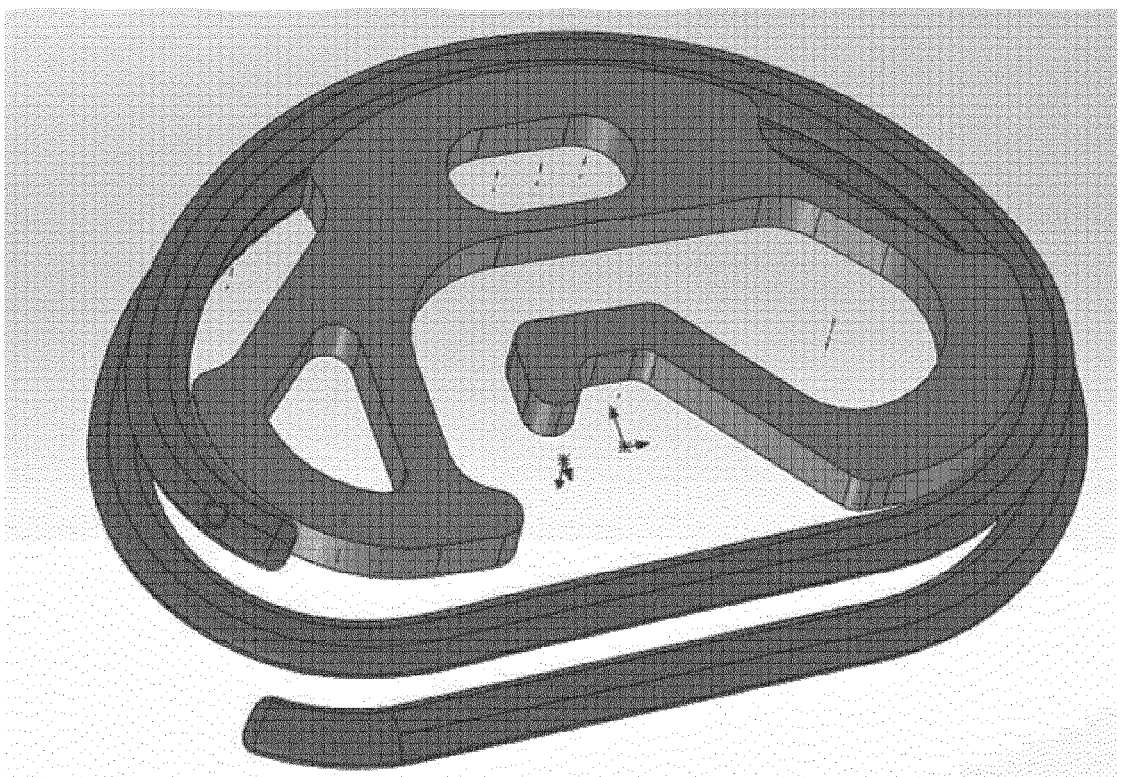

FIGS. 15a-b—discloses a medical device 1500 having a support 102 that has a further third grip section 140 partly parallel to the first grip section 128, thereby forming an aperture 141 between aforementioned grip sections 128, 140. This may allow further versatility in achieving the correct grip at a certain stage during an insertion procedure. Further, this provides a further mode for providing the support 102 in the compressed configuration, by contacting and compressing a third engagement surface 142 at the third grip section 140 in first direction towards the first engagement surface 108 of the opposite free end 106. In addition, the free end 106 can be compressed towards second engagement surface 109 in a second direction, substantially perpendicular to the aforementioned first direction. The free end 106 may have an aperture or an angled portion to allow for engagement and compression with a tool in more than one direction.

Figure 16A:
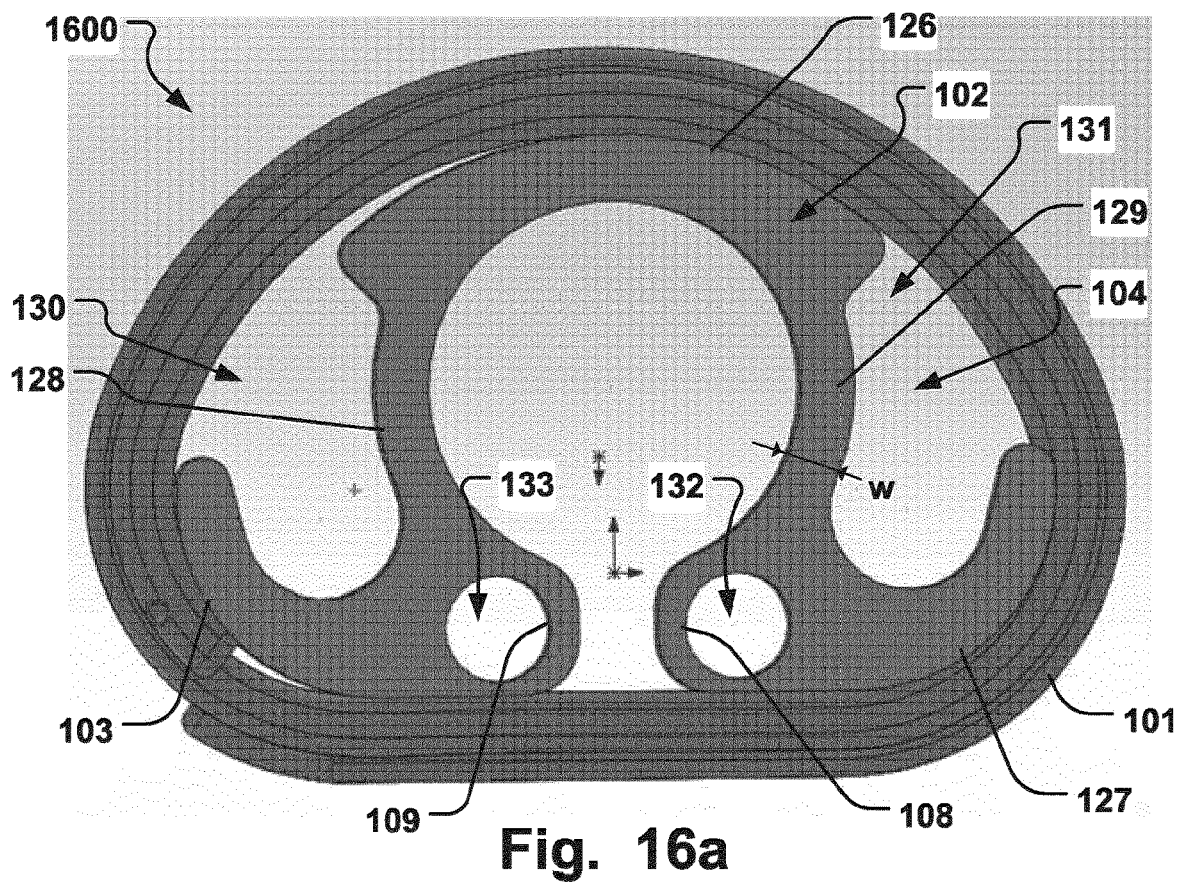
FIGS. 16a-b are illustrations of a medical device according to an embodiment of the invention holding a cardiac valve implant in place, where (a) is a top-down view and (b) is a perspective view.
Figure 16B:
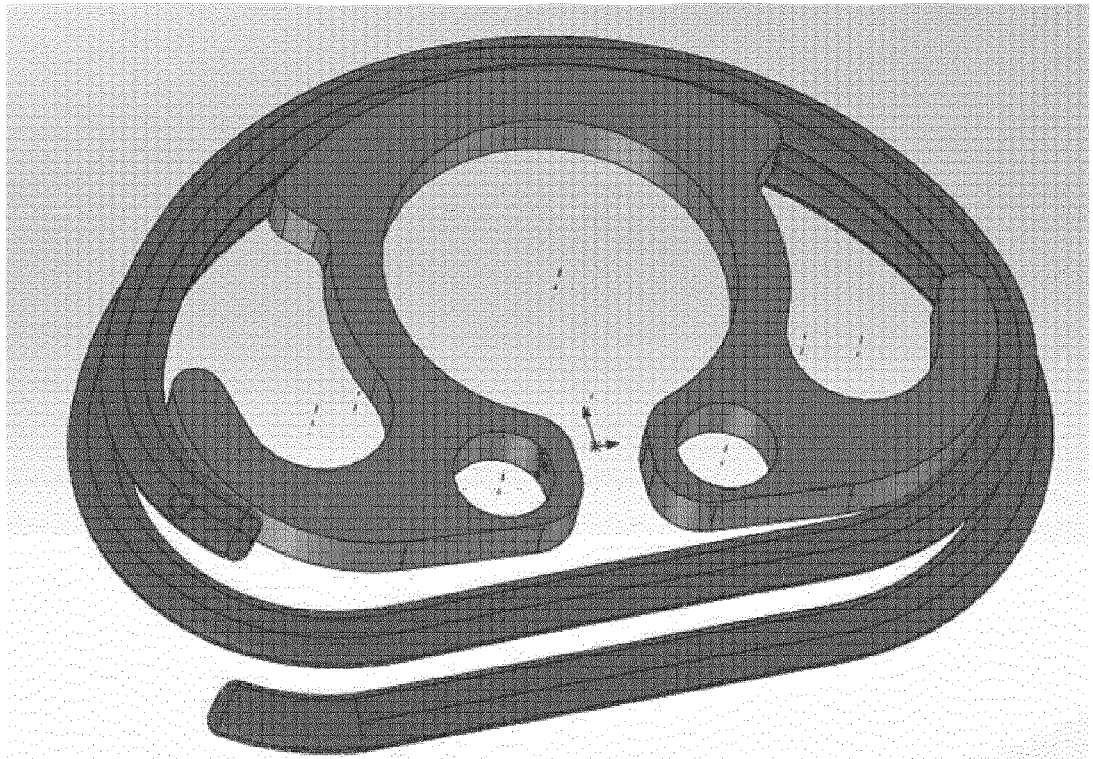

FIGS. 16a-b illustrates a further embodiment of a medical device 1600 according to an embodiment of the invention. The grip sections 128, 129 are displaced further inwards from the peripheral edges 103, 126, 127, of the support 102. Increased view at the peripheral edges is thus provided. Solid temporary hold of the implant 101 is still provided by the engagement surfaces 103, 127, that extend along sections of the interior of the implant. The grip sections 128, 129, may also be shaped to allow for optimized path of movement of the support 102 when compressed and expanded, e.g. curved grip sections 128, 129, as seen in FIGS. 16a-b.

Figure 17A:
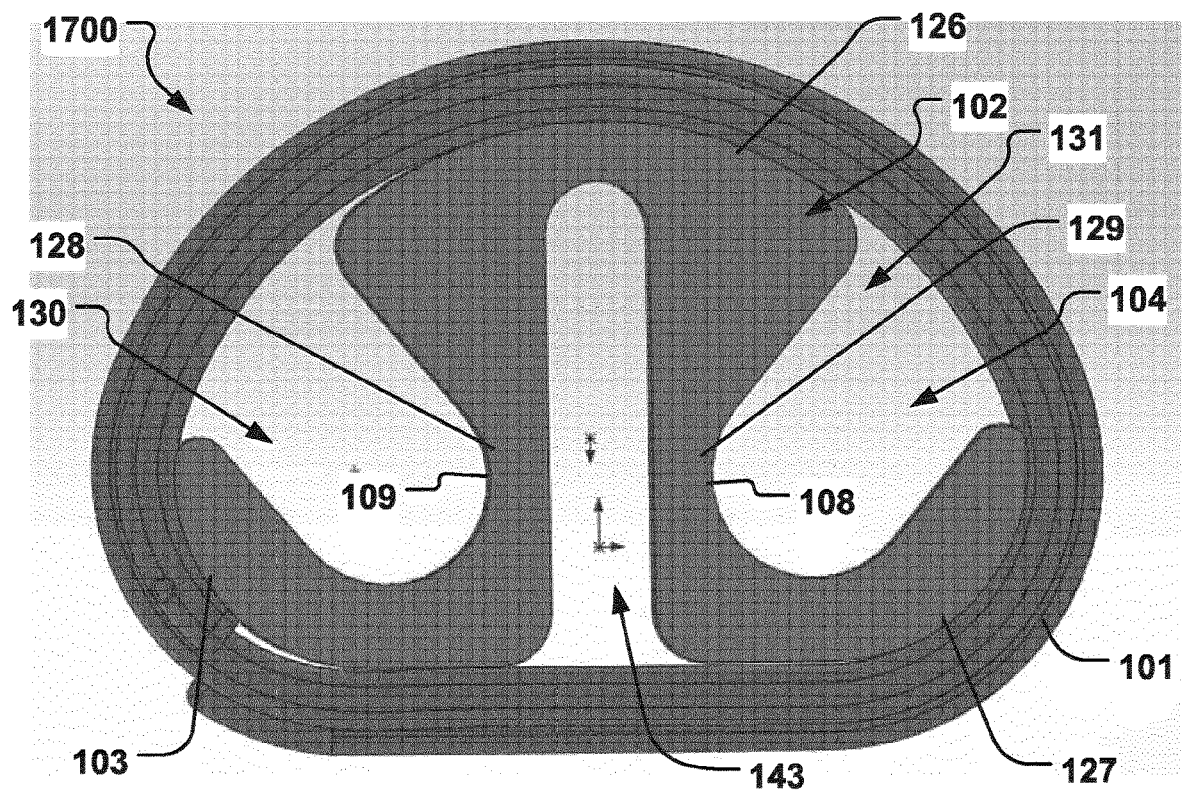
FIGS. 17a-b are illustrations of a medical device according to an embodiment of the invention holding a cardiac valve implant in place, where (a) is a top-down view and (b) is a perspective view.
Figure 17B:
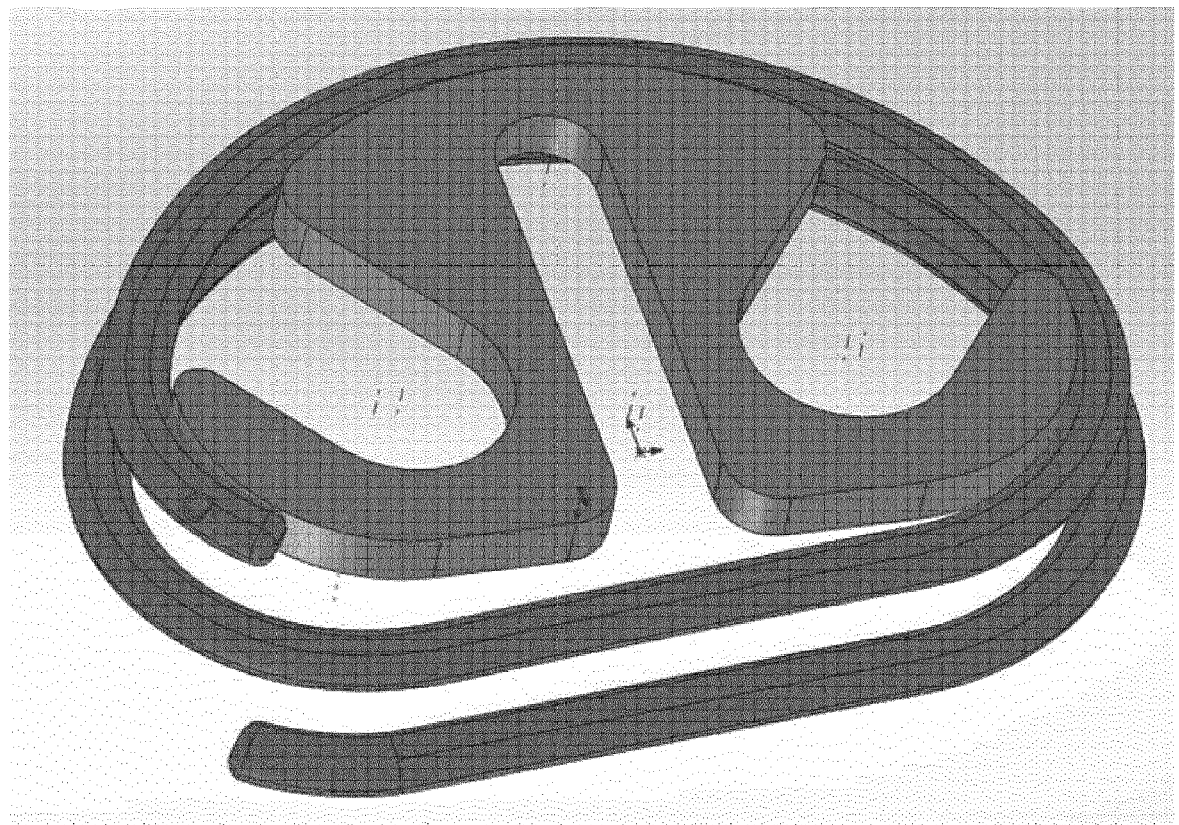

FIGS. 17a-b illustrates a further embodiment of a medical device 1700 according to an embodiment of the invention. The grip sections 128, 129, form an elongate opening 143 in the central portion of the device 1700. The shape of the support 102 may be optimized to allow for particularly easy manufacturing. First and second engagement surfaces 108, 109, may be compressed towards each other, as in the previously described embodiments.

Figure 18A:
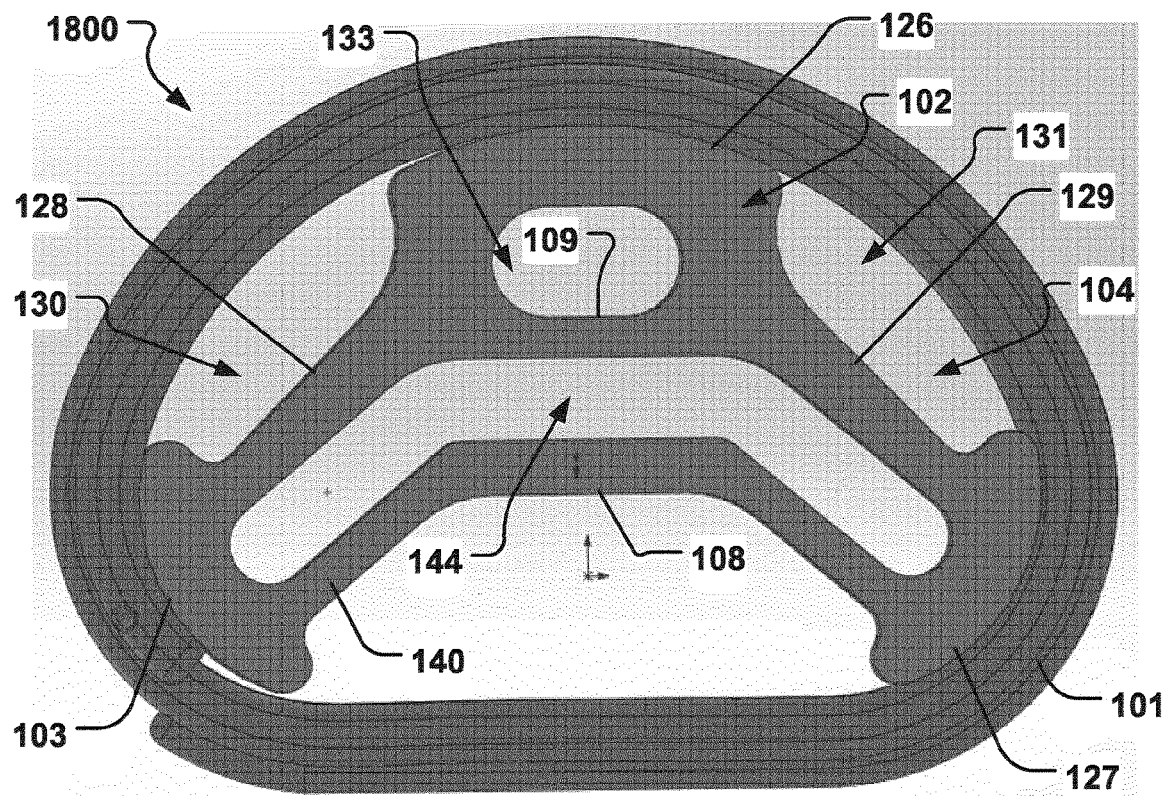
FIGS. 18a-b are illustrations of a medical device according to an embodiment of the invention holding a cardiac valve implant in place, where (a) is a top-down view and (b) is a perspective view.
Figure 18B:
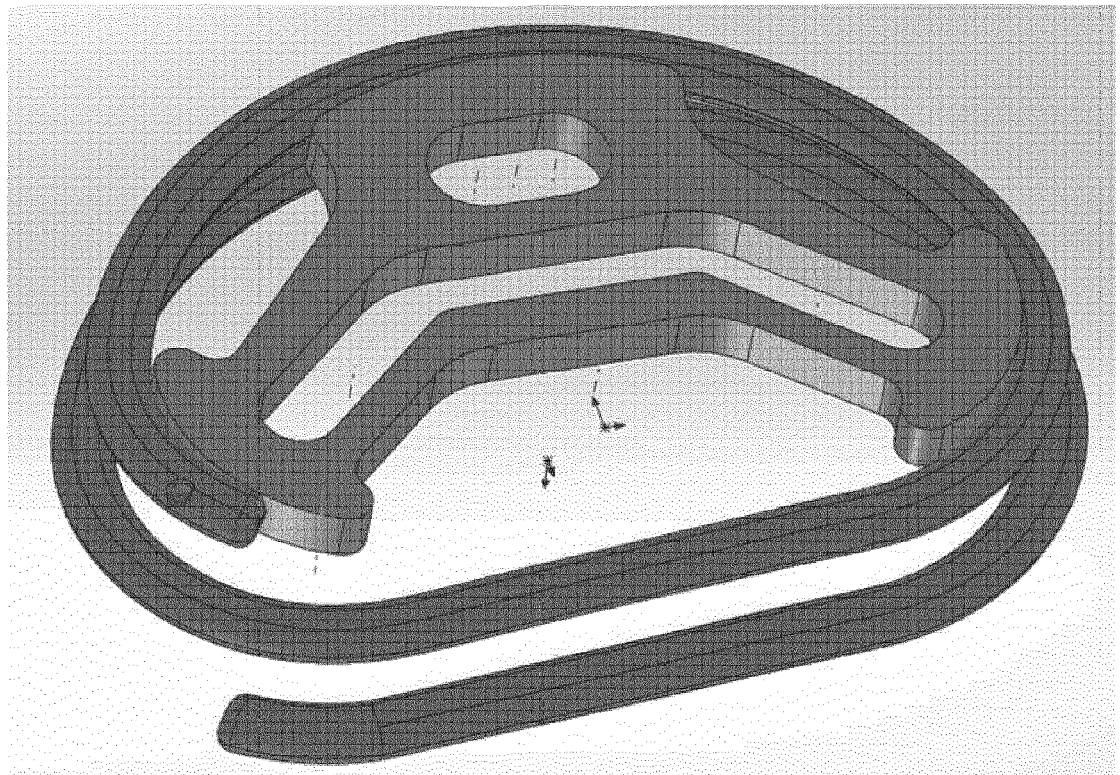

The device 1800 illustrated in FIGS. 18a-b according to another embodiment of the invention comprise an elongate aperture 144 formed by the boundaries of the first, second and third grip section 103, 128, 129. The third grip section 140 may comprise the engagement surface 108 for being compressed towards the opposite second engagement surface 109, whereby the peripheral edges 103, 127, connected with the third grip section 140 are moved towards each other and inwards in a direction towards a center of the support 102, in order to release from the implant 101.

Figure 19A:
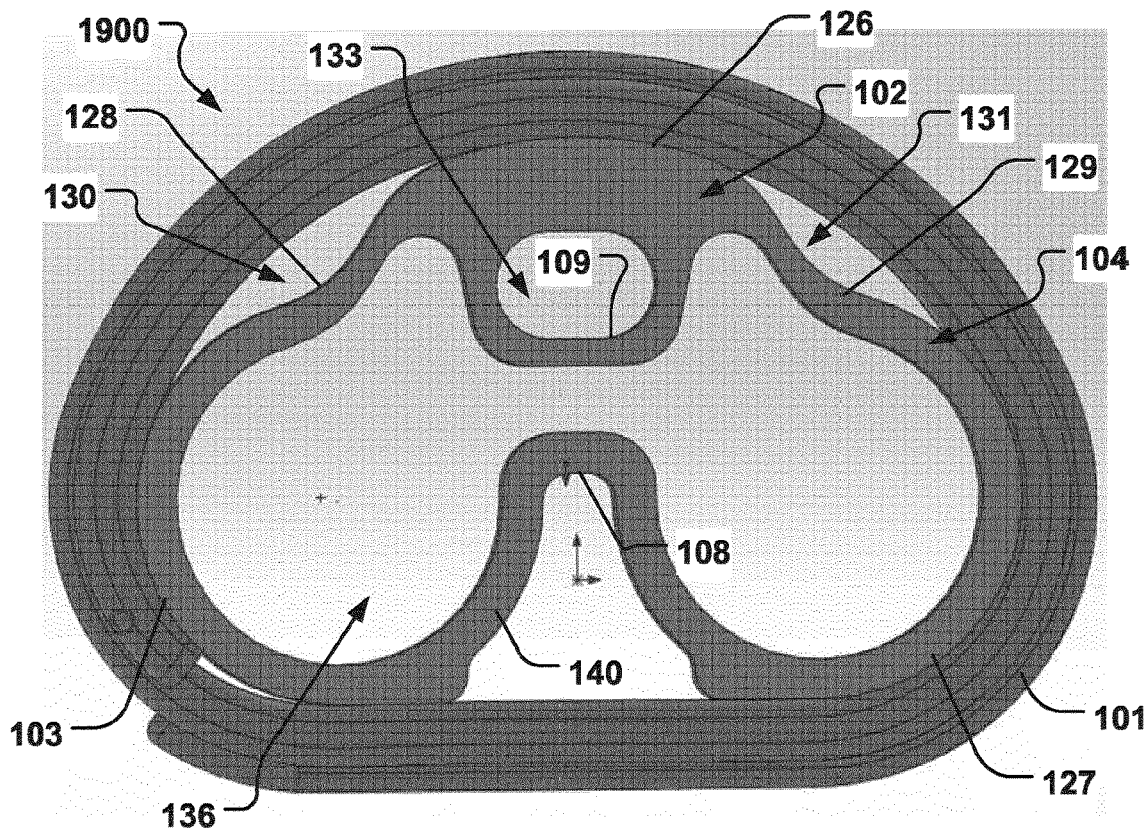
FIGS. 19a-b are illustrations of a medical device according to an embodiment of the invention holding a cardiac valve implant in place, where (a) is a top-down view and (b) is a perspective view.
Figure 19B:

FIGS. 19a-b illustrates a device 1900 according to another embodiment of the invention, where the peripheral edges 103, 127, of the support 102 are partly spherical, oval, or in a shape that conforms to the implant 101 over a substantial portion of the circumference of the implant 101. The engagement surface 108 is provided at a bridge between the oval portions, and when compressed in a direction towards the opposite second engagement surface 109, the circumference of either of the oval portions decreases in order to release the support 102 from the implant 101. The embodiment provides for a support which comes into apposition with increased length of the inside circumference of the implant 101, while still providing grip sections 128, 129, 140, at the periphery of the support 102 for multiple choices of manipulation points during a positioning procedure.

Figure 20A:
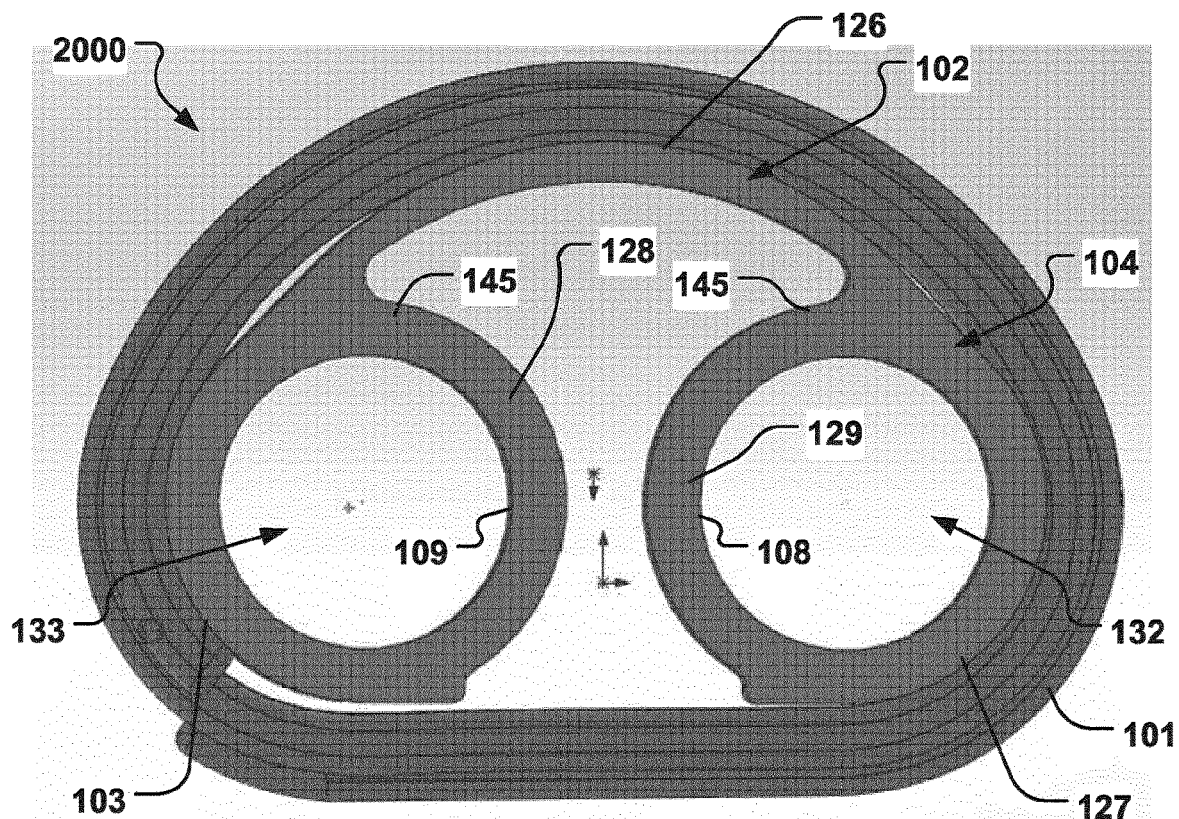
FIGS. 20a-b are illustrations of a medical device according to an embodiment of the invention holding a cardiac valve implant in place, where (a) is a top-down view and (b) is a perspective view.
Figure 20B:
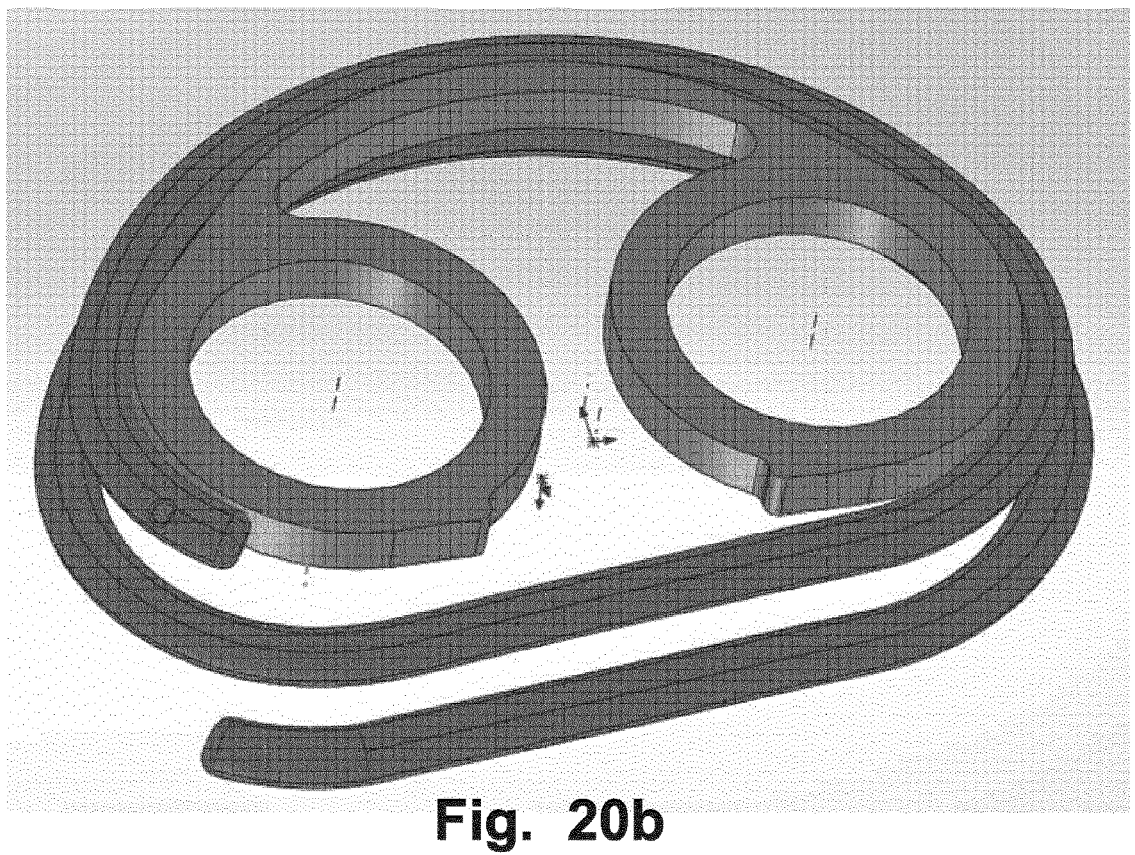

The device 2000 in FIGS. 20a-b has two oval or circular portions 145, defining apertures 132, 133, for manipulation, e.g. via curved grip section 128 which forms one of the apertures 133. The oval portions of the support 102 define both the peripheral edges 103, 127, that conform to the implant 101 and the grip sections 128, 129. The oval portions 145 can be compressed towards each other by pressing engagements surfaces 108, 109, at the inside surface of the oval portions.

Figure 21A:
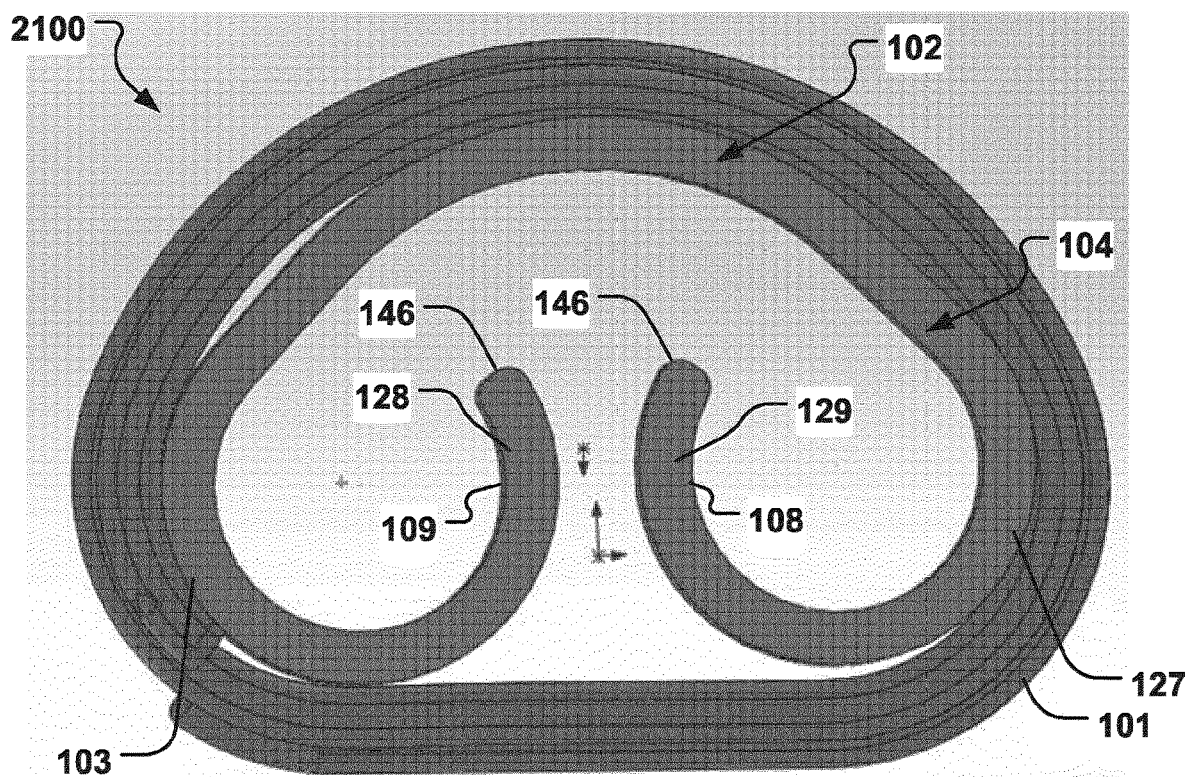
FIGS. 21*a-b* are illustrations of a medical device according to an embodiment of the invention holding a cardiac valve implant in place, where (a) is a top-down view and (b) is a perspective view.
Figure 21B:
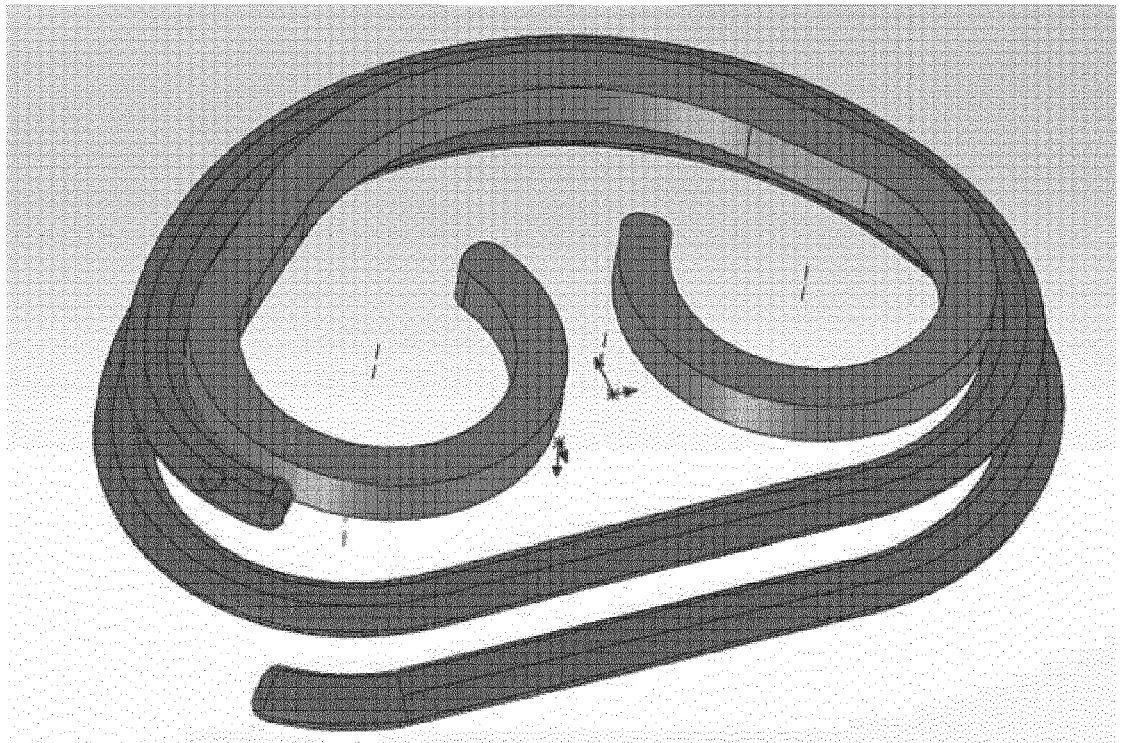

The device 2100 in FIGS. 21a-b is similar to the device 2000 in FIGS. 20a-b, but the oval portions are open, thereby forming free ends 146, forming substantially semi-circular portions of the support 102 that comprise the engagement edges 103, 127. As in FIGS. 20a-b the semi-circular portions functions as grip sections 128, 129, for a tool to e.g. twist, push or pull the support 102 and thereby the implant 101, and as engagement portions 108, 109, for manipulating the size of the support 102, and further as portions of the support 102 that conforms to the implant 101, i.e. via the peripheral edges 103, 127.

FIGS. 22a-d illustrates a gripper tool 400 according to an embodiment of the invention, that comprises a first and second grip member 401, 402, that are moveable in relation to each other to thereby clamp a grip section 128, 129, 140, of the medical device 1300-2100. The first and second grip members 401, 402 may be pivotable around a common pivoting point 403 in order to be movable in relation to each other and provide the clamping action to hold the support 102 of the medical device 1300-2100 in place. The first and second grip members 401, 402, may have a suitable groove along the distal edges of the grip members to conform to the curvature of the support 102 for a solid hold. The grip tool 400 may be used as a combination tool, likewise as described for tool 200, and can thereby both grip the grip sections 128, 129, 140, to manipulate the implant 101 once the support 102 holds the implant in place, and to change the shape of the support 102 by engaging the engagement surfaces 108, 109, to attach or release the support 102 from the implant 101.

FIG. 23 illustrates a method of manufacturing 500 a medical device for holding a cardiac valve implant 101, such as a device 1300-2100. The method comprises providing 501 a sheet of bulk material such as a polymer material, and providing 502 a template of the medical device, and further punching 503 the sheet with the template to provide the medical device, which medical device comprises a support 102 defining first and second peripheral edges 103, 126, each with a curvature about which the cardiac valve implant 101 can be fitted, and a grip section 128 for engagement with a gripper tool 400 in use of the support 102.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical device for holding a cardiac valve implant, said medical device comprising:
   a support defining first and second peripheral edges each with a curvature about which said cardiac valve implant can be fitted, wherein said support comprises:
   a flexible grip section positioned between and connecting said first and second peripheral edges at opposite sides of said flexible grip section, said flexible grip section defining an opening for engagement with a gripper tool in use of said support, wherein said flexible grip section is recessed inwards relative to said first and second peripheral edges and thereby defines said opening between said support and said cardiac valve implant when said cardiac valve implant is held in place by said support;
   wherein said flexible grip section forms a resilient portion of the support for resiliently holding said cardiac valve implant in place in said medical device;
   wherein said support has an expanded circumference (C) in a first configuration, and a reduced circumference (C') in a second configuration;
   wherein a flexing of the flexible grip section allows a relative motion between said first and second peripheral edges and thereby a radial movement of said support between said second configuration and said first configuration; and
   wherein said flexing of said flexible grip section occurs essentially in a plane of said support.

2. The medical device according to claim 1, further comprising a third peripheral edge with a curvature about which said cardiac valve implant can be fitted, said third peripheral edge being connected to either of said first and second peripheral edges by a second grip section.

3. The medical device according to claim 1, comprising a first engagement surface adapted to receive a tool for compressing said first engagement surface towards an opposite second engagement surface of said support in a compressed second configuration.

4. The medical device according to claim 1, wherein said support comprises two free ends, wherein one of said free ends comprises a first engagement surface adapted to receive a tool for compressing one of said free ends towards an opposite second engagement surface of said support in a compressed second configuration.

5. The medical device according to claim 1, wherein said support comprises two free ends, wherein the curvature of said first and second peripheral edges generally follows a three-dimensional path such that said free ends are axially off-set.

6. The medical device according to claim 3, wherein at least one of said first and second engagements surfaces are defined by the inside surface of an engagement aperture.

7. The medical device according to claim 1, wherein the entire support is flexible to allow a radial movement of said support between said second configuration and said first configuration.

8. The medical device according to claim 1, wherein the width (W) of said flexible grip section is chosen to set a predetermined spring force constant of said support.

9. The medical device according to claim 1, wherein said support is comprised of a monolithic piece of a polymer material.

10. The medical device according to claim 1, wherein said medical device further comprises a locking mechanism for fixating said support in a first expanded configuration.

11. The medical device according to a claim 1, wherein said support comprises a radially outwardly opening or groove along said first or second peripheral edge dimensioned to receive said cardiac valve implant.

12. The medical device according to claim 1, wherein the curvature of said first and second peripheral edges generally follows a three-dimensional path such that said curvature conforms to said cardiac valve implant extending in a corresponding three-dimensional path.

13. The medical device according to claim 1, wherein said support further comprises a friction reducing sheath along said first or second peripheral edge and extending in a radial direction to cover a portion of said cardiac valve implant when held in place by said medical device.

14. The medical device of claim 1, wherein said support comprises a total of three peripheral edges and said flexible grip section and a second grip section.

15. The medical device of claim 14, wherein a least one of said flexible grip section and the second grip section extends parallel to a portion of said cardiac valve implant.

16. A kit comprising the medical device according to claim 1, and a tool comprising a grip member arranged for gripping the flexible grip section of said medical device.

17. A medical device for holding a cardiac valve implant, said medical device comprising:
   a support defining first and second peripheral edges each with a curvature about which said cardiac valve implant can be fitted, wherein said support comprises:
   a flexible grip section positioned between and connecting said first and second peripheral edges at opposite sides of said flexible grip section, said flexible grip section defining an opening for engagement with a gripper tool in use of said support, wherein said flexible grip section is recessed inwards relative to said first and second peripheral edges and thereby defines said opening between said support and said cardiac valve implant when said cardiac valve implant is held in place by said support;
   wherein:
   said flexible grip section forms a resilient portion of the support for resiliently holding said cardiac valve implant in place in said medical device;
   said support has an expanded circumference (C) in a first configuration, and a reduced circumference (C') in a second configuration;
   a flexing of the flexible grip section allows a relative motion between said first and second peripheral edges and thereby a radial movement of said support between said second configuration and said first configuration; and said flexing of said flexible grip section occurs in a plane spanned by said curvature about which said cardiac valve implant can be fitted.

\* \* \* \* \*